US012582387B2

(12) United States Patent
Yamamoto et al.

(10) Patent No.: US 12,582,387 B2

(45) Date of Patent: Mar. 24, 2026

---

(54) ULTRASOUND DIAGNOSTIC SYSTEM AND OPERATION METHOD OF ULTRASOUND DIAGNOSTIC SYSTEM

(71) Applicant: FUJIFILM Corporation, Tokyo (JP)

(72) Inventors: Katsuya Yamamoto, Kanagawa (JP); Yasuhiko Morimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 27 days.

(21) Appl. No.: 18/604,526

(22) Filed: Mar. 14, 2024

(65) Prior Publication Data

US 2024/0225614 A1     Jul. 11, 2024

Related U.S. Application Data

(63) Continuation of application No. PCT/JP2022/031869, filed on Aug. 24, 2022.

(30) Foreign Application Priority Data

Sep. 21, 2021    (JP) ................................. 2021-153281

(51) Int. Cl.
| | |
|---|---|
| *A61B 8/00* | (2006.01) |
| *A61B 8/08* | (2006.01) |
| *A61B 8/12* | (2006.01) |

(52) U.S. Cl.
CPC .................. *A61B 8/56* (2013.01); *A61B 8/12* (2013.01); *A61B 8/4488* (2013.01);
(Continued)

(58) Field of Classification Search
CPC ........... A61B 8/56; A61B 8/12; A61B 8/4488; A61B 8/5223; A61B 8/54; A61B 8/58;
(Continued)

(56) References Cited

U.S. PATENT DOCUMENTS

| | | | |
|---|---|---|---|
| 6,210,335 B1 * | 4/2001 | Miller | ................. G01S 7/52046 |
| | | | 600/454 |
| 8,866,366 B2 | 10/2014 | Nakazawa et al. | |

(Continued)

FOREIGN PATENT DOCUMENTS

| | | |
|---|---|---|
| EP | 3586980 | 1/2020 |
| JP | 2001198124 | 7/2001 |

(Continued)

OTHER PUBLICATIONS

"International Search Report (Form PCT/ISA/210) of PCT/JP2022/031869", mailed on Oct. 4, 2022, with English translation thereof, pp. 1-5.

(Continued)

*Primary Examiner* — Alexei Bykhovski

(74) *Attorney, Agent, or Firm* — JCIPRNET

(57) ABSTRACT

Provided are an ultrasound diagnostic system capable of performing a polarization process of an ultrasound transducer using an existing transmission circuit and continuing examination of an observation target part while maintaining performance without degrading a workflow in a pause period after a transmission of a transmission signal consisting of an excitation pulse, and an operation method of an ultrasound diagnostic system.

As a result, a control circuit of an ultrasound diagnostic system controls such that an ultrasound generating transmission signal and a polarization process transmission signal are generated, after a transmission of the transmission signal, which generates an ultrasonic wave including at least an excitation ultrasonic wave that generates an acoustic radiation pressure, sets a polarization process time within a pause period according to an acoustic output value generated in a case of transmissions of the ultrasound generating transmission signal and the polarization process transmission signal, and controls a transmission circuit to transmit the polariza- (Continued)

tion process transmission signal to a plurality of ultrasound transducers that have transmitted at least the excitation ultrasonic waves, to perform the polarization process in the polarization process time.

20 Claims, 12 Drawing Sheets

(52) U.S. Cl.
CPC .............. *A61B 8/5223* (2013.01); *A61B 8/54* (2013.01); *A61B 8/58* (2013.01)

(58) Field of Classification Search
CPC ......... A61B 1/05; A61B 1/0005; A61B 1/273; A61B 1/31; A61B 8/445; A61B 8/4494; A61B 8/488; A61B 8/08; A61B 8/085; A61B 8/485; A61B 8/5207; G01S 7/5202; G01S 7/5205; G01S 15/8915; G01S 7/52042; G01S 7/52074
See application file for complete search history.

(56) References Cited

U.S. PATENT DOCUMENTS

| | | | |
|---|---|---|---|
| 11,737,731 | B2 | 8/2023 | Yamamoto et al. |
| 2004/0102703 | A1 | 5/2004 | Behren et al. |
| 2016/0213352 | A1* | 7/2016 | Toji ........................ A61B 8/485 |
| 2018/0156904 | A1 | 6/2018 | Owen et al. |
| 2020/0000438 | A1 | 1/2020 | Yamamoto et al. |
| 2020/0000439 | A1* | 1/2020 | Satoh ....................... A61B 8/58 |
| 2020/0025897 | A1* | 1/2020 | Borot ................. G01S 7/52046 |
| 2021/0015466 | A1 | 1/2021 | Weichenberger et al. |
| 2023/0000471 | A1 | 1/2023 | Yamamoto et al. |
| 2023/0346349 | A1 | 11/2023 | Yamamoto et al. |

FOREIGN PATENT DOCUMENTS

| | | |
|---|---|---|
| JP | 2013005137 | 1/2013 |
| JP | 2016137130 | 8/2016 |
| JP | 2017143353 | 8/2017 |
| JP | 2018519052 | 7/2018 |
| JP | 2020000601 | 1/2020 |
| JP | 2020000625 | 1/2020 |

OTHER PUBLICATIONS

"Written Opinion of the International Searching Authority (Form PCT/ISA/237) of PCT/JP2022/031869", mailed on Oct. 4, 2022, with English translation thereof, pp. 1-8.
"Search Report of Europe Counterpart Application", issued on Dec. 12, 2024, p. 1-p. 8.
Cho-Chiang Shih et al., "Evaluating the intensity of the acoustic radiation force impulse (ARFI) in intravascular ultrasound (IVUS) imaging: Preliminary in vitro results", Ultrasonics, vol. 70, Apr. 2016, pp. 64-74.

* cited by examiner

FIG. 4

FIG. 5
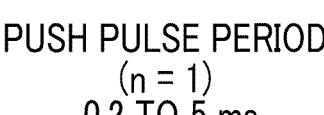 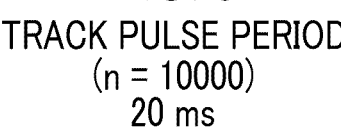
PUSH PULSE PERIOD
(n = 1)
0.2 TO 5 ms
TRACK PULSE PERIOD
(n = 10000)
20 ms
POLARIZATION
PROCESS PERIOD
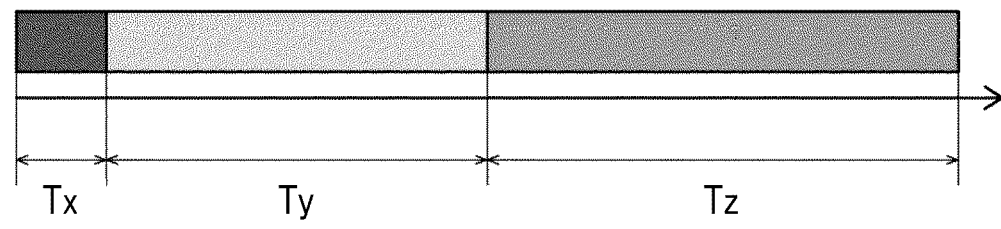
Tx          Ty          Tz
FIG. 6A
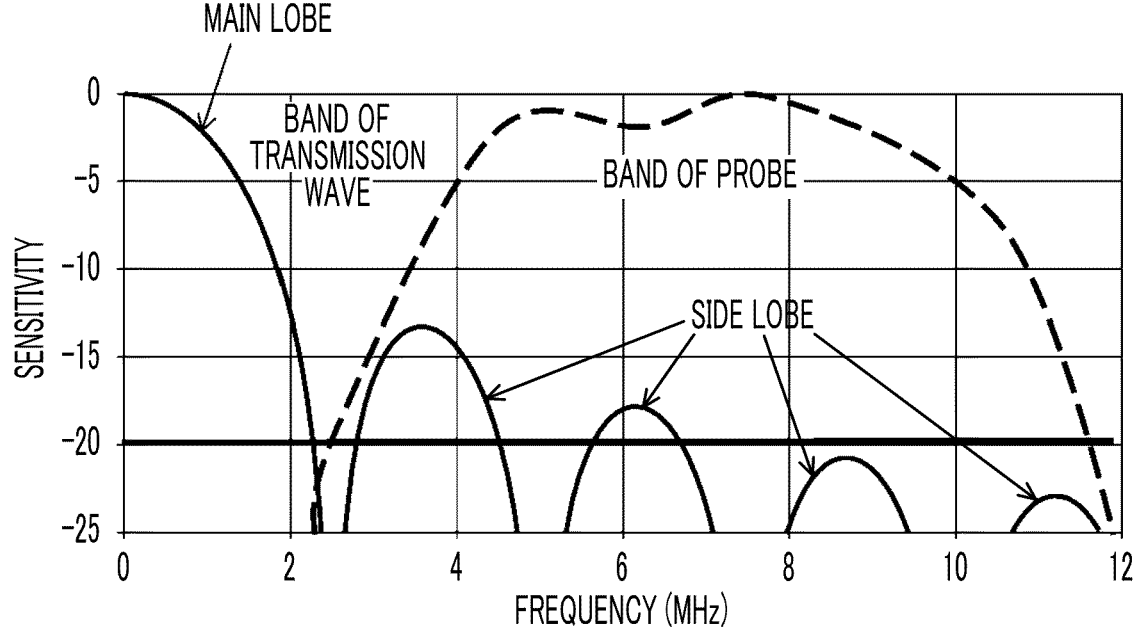
FIG. 6B

FIG. 11

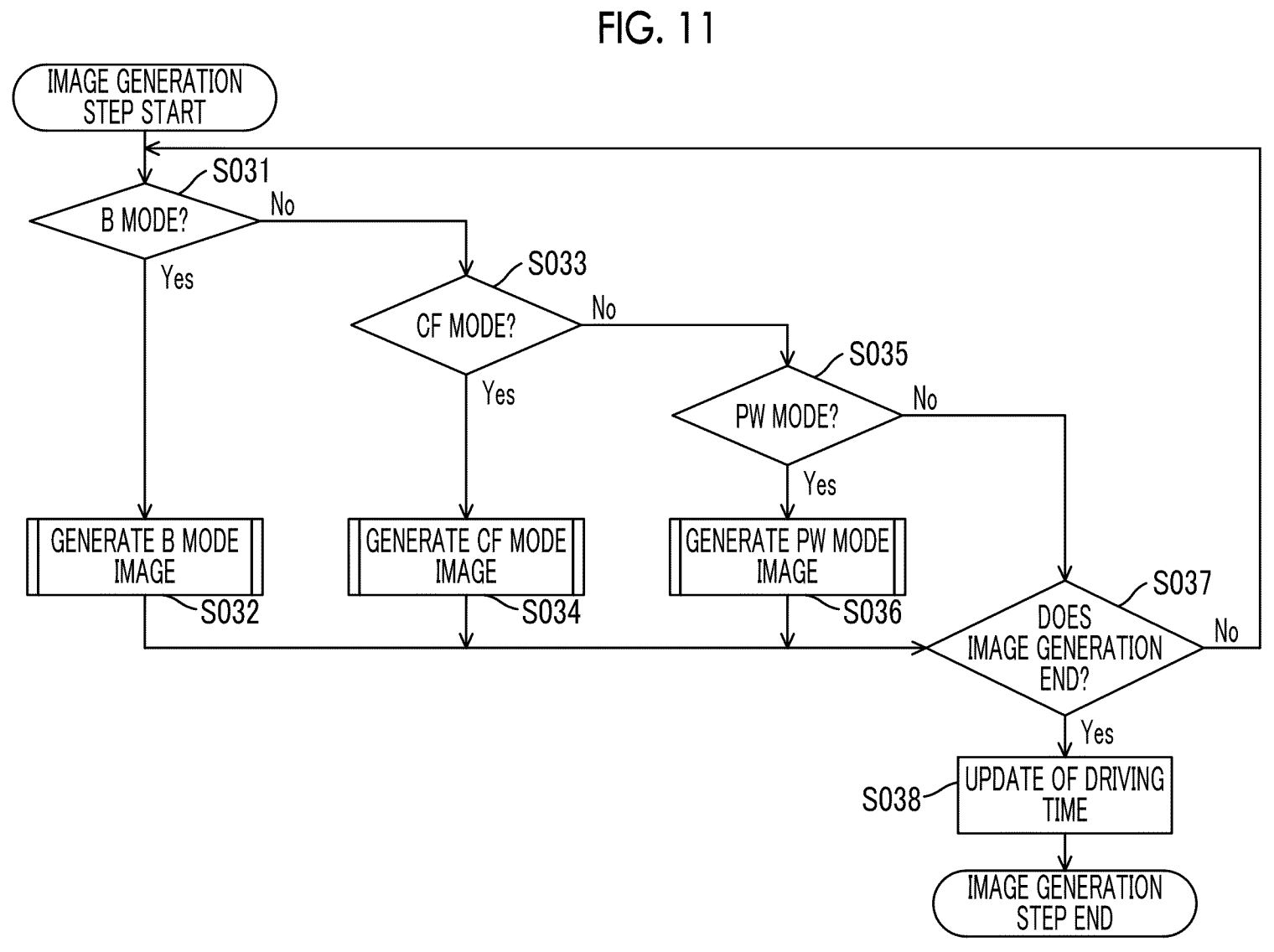

IMAGE GENERATION STEP START

S031
B MODE?

Yes → GENERATE B MODE IMAGE — S032

No →

S033
CF MODE?

Yes → GENERATE CF MODE IMAGE — S034

No →

S035
PW MODE?

Yes → GENERATE PW MODE IMAGE — S036

No →

S037
DOES IMAGE GENERATION END?

No →

Yes → UPDATE OF DRIVING TIME — S038

IMAGE GENERATION STEP END

FIRST DISPLAY MODE

ULTRASOUND IMAGE

SECOND DISPLAY MODE

ULTRASOUND IMAGE

ENDOSCOPE IMAGE

THIRD DISPLAY MODE

ENDOSCOPE IMAGE

ULTRASOUND IMAGE

FOURTH DISPLAY MODE

ENDOSCOPE IMAGE

P3

P2

P3

P1

48

PUSH PULSE
(n = 1)
0.2 TO 5 ms

TRACK PULSE
(n = 10000)
20 ms

FREEZE 1          2                    3

ULTRASOUND DIAGNOSTIC SYSTEM AND OPERATION METHOD OF ULTRASOUND DIAGNOSTIC SYSTEM

CROSS-REFERENCE TO RELATED APPLICATIONS

This application is a Continuation of PCT International Application No. PCT/JP2022/031869 filed on Aug. 24, 2022, which claims priority under 35 U.S.C. § 119(a) to Japanese Patent Application No. 2021-153281 filed on Sep. 21, 2021. The above applications are hereby expressly incorporated by reference, in their entirety, into the present application.

BACKGROUND OF THE INVENTION

1. Field of the Invention

The present invention relates to an ultrasound diagnostic system, which performs a polarization process on a plurality of depolarized ultrasound transducers in a case of performing ultrasonic elastography for evaluating a hardness of a tissue of an observation target part, and an operation method of an ultrasound diagnostic system.

2. Description of the Related Art

As an ultrasound diagnostic system for the purpose of biliary-pancreatic observation using the transgastrointestinal tract, an ultrasound endoscope in which an ultrasound observation portion is provided at the distal end portion of an endoscope is used. Such an ultrasound diagnostic system acquires an ultrasound image of the inside of a body cavity of a subject by transmitting and receiving ultrasonic waves by driving a plurality of ultrasound transducers inside the body cavity of the subject. In the ultrasound diagnostic system, it is necessary to avoid a reduction in sensitivity in a state in which the ultrasound diagnostic system is placed inside the body cavity of the subject.

In the ultrasound diagnostic system, the plurality of ultrasound transducers are, for example, single crystal transducers that are piezoelectric elements, and are usually used in a polarized state. The ultrasound transducer that is a single crystal transducer can receive ultrasonic waves with high sensitivity, but a depolarization phenomenon in which the degree of polarization decreases as the driving time increases may occur. In a case where a depolarization phenomenon occurs, the reception sensitivity of the ultrasound transducer decreases, which may affect the image quality of the ultrasound image. For this reason, as a measure against depolarization of the single crystal transducer, restoring the sensitivity by performing a repolarization process (hereinafter, also simply referred to as polarization process) is also known.

The risk of depolarization is correlated with the thickness of the transducer, that is, the resonance frequency of the transducer. The risk decreases as the thickness of the transducer increases (as the frequency of the transducer decreases). For this reason, the risk of depolarization is avoided by using a transducer using a single crystal transducer for body surface in a low frequency band of 1 to 6 MHZ.

On the other hand, in the case of transmitting and receiving ultrasonic waves by driving each ultrasound transducer inside the body cavity of the subject, since it is necessary to set the frequency of the ultrasonic wave to a high frequency band of 7 to 8 MHz level, a transducer having a relatively small thickness is used. However, as the thickness of the transducer decreases, the risk of occurrence of a depolarization phenomenon increases. Therefore, in the case of a thin transducer, a process of repolarization is required.

For this reason, techniques for countermeasures against depolarization in the ultrasound diagnostic apparatus have been developed so far. For example, an ultrasound sensor as a piezoelectric sensor apparatus described in JP2013-005137A (JP5874208B) has a piezoelectric element having a piezoelectric body and a pair of electrodes interposing the piezoelectric body therebetween, a detection circuit for performing detection process for detecting a detection signal output from the piezoelectric element, and a dedicated polarization process circuit for performing polarization process by applying a polarization voltage to the piezoelectric element. In the ultrasound sensor described in JP2013-005137A (JP5874208B) having such a configuration, it is possible to restore polarization by detecting depolarization from a difference in characteristics between the piezoelectric elements using the detection circuit and performing polarization process using the dedicated polarization process circuit. The polarization process is performed at a timing at which the electric power is supplied, a timing at which a request signal for performing detection process is input (each reception timing), or a timing at which a predetermined standby transition time has passed after the end of detection process, for example. Therefore, even in a case where a depolarization phenomenon occurs in the piezoelectric element, the piezoelectric element can be polarized again. As a result, it is possible to maintain the reception sensitivity of the piezoelectric element.

As another example, the ultrasound sensor described in JP2017-143353A has a piezoelectric element and a driving circuit for driving the piezoelectric element. The driving circuit drives the piezoelectric element with a driving waveform having, first, a step of maintaining the polarization of the piezoelectric element with a first potential V1, next, a step of transmitting an ultrasonic wave to the piezoelectric element by applying a maximum potential VH and a minimum potential VL at least once, next, a step of causing the piezoelectric element to stand by at a second potential V2, next, a step of increasing the second potential V2 to a third potential V3, next, a step of maintaining the third potential V3 while the piezoelectric element receives an ultrasonic wave, and next, a step of returning the third potential V3 to the first potential V1. In the ultrasound diagnostic apparatus described in JP2017-143353A having such a configuration, it is possible to drive the piezoelectric element while maintaining the polarization of the piezoelectric element by driving the piezoelectric element with the driving waveform having the above-described six steps. That is, JP2017-143353A describes that depolarization is prevented by studying the waveform for driving the piezoelectric element.

In addition, the ultrasound diagnostic apparatus described in JP2020-000601A and JP2020-000625A comprises an ultrasound endoscope including an ultrasound observation portion, which transmits an ultrasonic wave to a subject and receives a reflected wave of the ultrasonic wave by using an ultrasound transducer array, and an ultrasound processor device that generates an ultrasound image based on a reception signal, in which the ultrasound processor device includes a control circuit that performs a polarization process on a plurality of ultrasound transducers in a non-diagnosis period in which the transmission of the ultrasonic wave for performing ultrasound diagnosis and the reception of the reflected wave are not performed. In the ultrasound system described in JP2020-000601A or JP2020-000625A having such a configuration, polarization process of ultrasound transducers using an existing transmission circuit for transmitting a transmission signal to ultrasound transducers of an ultrasound endoscope, in a non-diagnosis time different from a time for acquiring an ultrasound image, without affecting the image quality of the ultrasound image and without causing a significant change in the existing circuit configuration and an increase in the circuit size.

Meanwhile, as a method of evaluating a hardness of a tissue in the related art, there is ultrasonic elastography that performs image diagnosis that evaluates the hardness of the tissue by deforming the tissue by an external force, estimating the hardness from the deformation, and imaging or quantifying the hardness of the tissue. In ultrasonic elastography using manual compression in the related art, strain elastography, which is a method in which an ultrasound probe is pressed against an observation target part to observe deformation such as movement of a tissue of an observation target on a B mode image, and a hardness of a tissue is evaluated based on the amount of deformation, such as those with small deformation being hard and those with large deformation being soft, is known. That is, the strain elastography is a method of observing a strain due to pressurization.

On the other hand, in recent years, in the strain elastography, acoustic radiation force impulse (ARFI) imaging, that is, ARFI elastography, which evaluates a hardness of a tissue by deforming a tissue of an observation target and measuring the displacement of the tissue using an ARFI, which is a physical phenomenon in which a force that pushes an object backward is generated by irradiation with ultrasonic wave, instead of physically pressing an ultrasound probe to deform the tissue of the observation target, is known.

In addition, for the strain elastography, shear wave (SW) imaging, that is, shear wave elastography (SWE), which evaluates a hardness of a tissue by using ARFI to generate a shear clastic wave (shear wave) in a tissue of an observation target and measuring a propagation velocity of the shear elastic wave, that is, an acoustic velocity, is known. That is, the shear wave elastography is a method of measuring the propagation velocity of the shear wave.

The ARFI imaging and the SW imaging are methods in which a strain of a tissue is generated by irradiation with a strong ultrasonic wave with an excitation pulse called a push pulse, and a hardness of the tissue is evaluated from a displacement amount of the tissue or an acoustic velocity of a shear wave generated in the tissue.

In addition, an ultrasound system described in JP2018-519052A includes an ultrasound probe having an array of ultrasound transducer elements, and a transmission beam former that has a transmission channel, which is coupled to the ultrasound transducer elements, and that applies an asymmetric transmission signal to the elements during each transmission interval. The ultrasound system drives elements of an ultrasound probe using an asymmetric transmission signal that enhances polling (polarization) of a probe transducer. In the ultrasound system described in JP2018-519052A having such a configuration, in a case where the elements of the ultrasound probe are used to generate a long-time high-energy pressure wave such as a shear wave push pulse for measuring a shear wave in a body, depolarization can be prevented by using an asymmetric waveform.

SUMMARY OF THE INVENTION

As described above, in the ultrasound sensor, the ultrasound apparatus, ultrasound diagnostic apparatus, and the ultrasound system described in JP2013-005137A (JP5874208B), JP2017-143353A, JP2020-000601A, JP2020-000625A, and JP2018-519052A, it is possible to repolarize and restore or maintain the polarization of the piezoelectric element formed of a piezoelectric body, the ultrasound transducer, the ultrasound transducer element of the ultrasound probe, and the like.

However, as in the ultrasound sensor described in JP2013-005137A (JP5874208B), providing a dedicated circuit for performing repolarization, a depolarization detection mechanism, and the like is a large hardware change factor. Accordingly, there is a problem in that it is very difficult to mount those described above in the existing system.

In the ultrasound sensor described in JP2017-143353A, in order to prevent depolarization and maintain polarization, the pulse length of the driving waveform is increased by inserting a DC component into each driving waveform. Accordingly, there is a problem in that the frame rate is reduced to affect the image quality of the ultrasound image. In addition, in order to prevent depolarization using such a driving waveform, there is a problem in that there is a tradeoff between the image quality and the risk of depolarization.

In addition, in the ultrasound diagnostic apparatus described in JP2020-000601A and JP2020-000625A, in a case where a diagnosis period for acquiring the ultrasound image is long or frequently provided, even in a case where a repolarization process can be performed during the non-diagnosis period, as a result, a period in which the ultrasound transducer performs the transmission of ultrasonic wave and the reception reflected wave becomes longer, and depolarization of the ultrasound transducer progresses. Accordingly, there is a problem in that it is necessary to provide a period in which the transmission of ultrasonic wave and the reception reflected wave by the ultrasound transducer are stopped and repolarization of the ultrasound transducer is performed.

In addition, since a transmission waveform different from that in image visualization is usually used in the repolarization process, the ultrasound output is weak. However, in the ultrasound apparatus or the like in the related art, there is a problem in that the frame rate decreases in a case where the repolarization process is performed during scanning.

Meanwhile, in an ultrasound system that performs ultrasonic elastography, in a case where an excitation pulse (hereinafter, also referred to as push pulse) is transmitted in a case of performing ARFI imaging and shear wave imaging, a strong ultrasonic wave is input to a tissue of an observation target in a short period of time. For a temporal average intensity that can be input to a living body, premarket notification 510(k) of the guidance of US Food and Drug Administration (FDA) specifies that an attenuated spatial peak temporal average intensity (Ispta.α) is set to 720 mW/cm² or less due to safety issues for a living body. 510(k) (https://www.fda.gov/media/71100/ download: Marketing Clearance of Diagnostic Ultrasound Systems and Transducers: marketing clearance of diagnostic ultrasound system and transducer)

Therefore, in a case where a strong ultrasound output is performed, it is necessary to include a pause period (freeze section) to reduce the attenuated spatial peak temporal average intensity (Ispta.α).

FIG. 13 shows an example in which a shear wave (SW) is used. After a transmission of a push pulse P1, transmission and reception of an ultrasonic wave (track pulse P2) for detecting a shear wave are performed, and then a pause period 3 begins. Here, a thick line shown on the left side of FIG. 13 indicates the transmission of the push pulse P1 to an ultrasound transducer (a piezoelectric element of the ultrasound transducer) 48, a one-dot chain line indicates the transmission of the track pulse P2, and a two-dot chain line indicates a reception of a reflected wave P3 of the track pulse P2. In addition, a push pulse transmission period 1 from a transmission of a single push pulse P1 (n=1) or a plurality of simultaneous push pulses P1 to start of the transmission of the track pulse P2 is 0.2 to 5 ms, and a track pulse transmission/reception period 2 from the start of the transmission of the track pulse P2 (n=10000) to end of the reception of the reflected wave P3 is 20 ms, and a period from the end of the reception of the reflected wave P3 of the track pulse P2 to start of a subsequent transmission of the push pulse P1 is the pause period 3.

On the other hand, in a case where an ultrasound transducer formed of a single crystal is used, an application of a strong voltage increases the risk of depolarization, so that it is necessary to quickly perform repolarization of the ultrasound transducer after the transmission of the push pulse. In the repolarization process, since the pulse driving is performed outside a band of the probe, there is almost no ultrasound output from the element (ultrasound transducer), and the influence on a temporal average intensity is also suppressed to be low.

As in the ultrasound system described in JP2018-519052A, even in a case where a transmission signal applied to the ultrasound transducer element includes a push pulse, the polarization of the ultrasound transducer element can be maintained by making the transmission signal asymmetric. However, an amplitude asymmetry of the signal waveform of the transmission signal generates a larger electric field in a direction of enhancing a polarization of a piezoelectric material and a smaller electric field in a direction of degrading the polarization of the piezoelectric material to enhance the polarization. For this reason, there is a problem in that it is necessary to select the amplitude asymmetry of the signal waveform by the polarization of the ultrasound transducer element.

In addition, in a case where the transmission signal including the push pulse is applied to the ultrasound transducer element, although the polarization can be maintained, the temporal average intensity exceeds the above-described limit value, and thus it is necessary to provide a pause period. Accordingly, there is also a problem in that workflow is degraded depending on the pause period according to the temporal average intensity.

An object of the present invention is, to solve the above-described problems of the related art and to examine a state such as a hardness of a tissue of the observation target part, to provide an ultrasound diagnostic system that is capable of performing a polarization process of an ultrasound transducer by using an existing transmission circuit that has transmitted a transmission signal, the transmission signal being an ultrasound generating transmission signal consisting of an excitation pulse capable of generating an ultrasonic wave including an excitation ultrasonic wave that generates an acoustic radiation pressure, in a pause period after the transmission of the transmission signal and that is capable of continuing examination of an observation target part while maintaining performance without degradation in workflow in the pause period, and an operation method of an ultrasound diagnostic system.

To achieve the above object, an ultrasound diagnostic system according to a first aspect of the present invention is an ultrasound diagnostic system that acquires an ultrasound image and evaluates a hardness of a tissue of a diagnosis target using an acoustic radiation pressure, the ultrasound diagnostic system comprising an ultrasound observation portion that transmits an ultrasonic wave including at least an excitation ultrasonic wave for exciting the tissue by the acoustic radiation pressure using an ultrasound transducer array in which a plurality of ultrasound transducers are arranged, and receives a reflected wave from the tissue; and an ultrasound processor device including a transmission circuit, which transmits an ultrasound generating transmission signal consisting of driving pulses to be applied to the plurality of ultrasound transducers to generate the ultrasonic waves from the plurality of ultrasound transducers, a reception circuit that outputs a reception signal of the reflected wave received by the plurality of ultrasound transducers, and an evaluation unit that evaluates the hardness of the tissue based on the reception signal, in which the ultrasound processor device further includes a control circuit that performs the transmission of the ultrasonic wave and the reception of the reflected wave and that performs a polarization process using the transmission circuit on the plurality of ultrasound transducers that have transmitted the ultrasonic waves, in a pause period of all transmissions of ultrasonic waves after the transmission of the ultrasonic wave, the control circuit controls the transmission circuit to generate the ultrasound generating transmission signal consisting of the driving pulse, controls the transmission circuit to generate a polarization process transmission signal to be transmitted to the plurality of ultrasound transducers, and after the transmission of the ultrasound generating transmission signal, which generates the ultrasonic wave including at least the excitation ultrasonic wave that generates the acoustic radiation pressure, sets a polarization process time for performing the polarization process within the pause period according to an acoustic output value generated in a case of the transmissions of the ultrasound generating transmission signal and the polarization process transmission signal, and the polarization process transmission signal is transmitted from the transmission circuit to the plurality of ultrasound transducers that have transmitted at least the excitation ultrasonic waves, to perform the polarization process in the polarization process time.

Here, it is preferable that the control circuit calculates the acoustic output value in the polarization process in response to an operation of a user on the tissue, and controls the polarization process time within the pause period such that the acoustic output value is equal to or less than a preset index value of acoustic output.

In addition, it is preferable that the control circuit calculates a level of depolarization of the plurality of ultrasound transducers generated by the transmission of the ultrasonic wave from a transmission time of the ultrasound generating transmission signal consisting of the driving pulse, calculates the acoustic output value in the polarization process from the calculated level of depolarization, and controls the polarization process time within the pause period according to the calculated acoustic output value.

In addition, it is preferable that the transmission circuit transmits a first transmission signal consisting of an excitation pulse as the ultrasound generating transmission signal to at least some of the plurality of ultrasound transducers, and generates the excitation ultrasonic waves from the plurality of ultrasound transducers and transmits the generated excitation ultrasonic waves to the tissue to press and displace the tissue, the reception circuit receives a first reception signal of the reflected wave from the tissue as the reception signal, the evaluation unit calculates the displacement of the tissue based on the ultrasound image obtained from the first reception signal to evaluate the hardness of the tissue, and 7 8 the pause period is a period from an end of the transmission of the first transmission signal to a start of a subsequent transmission of the first transmission signal.

In addition, it is preferable that the transmission circuit transmits a first transmission signal consisting of an excitation pulse as the ultrasound generating transmission signal to at least some of the plurality of ultrasound transducers, and generates the excitation ultrasonic waves from the plurality of ultrasound transducers and transmits the generated excitation ultrasonic waves to the tissue to press and displace the tissue, and then transmits a second transmission signal consisting of a detection pulse for detecting the displacement of the tissue to at least some of the plurality of ultrasound transducers to generate a detection ultrasonic wave, and transmits the generated detection ultrasonic wave to the tissue, the reception circuit receives a second reception signal of the reflected wave of the detection ultrasonic wave from the tissue as the reception signal, the evaluation unit calculates the displacement of the tissue based on the ultrasound image obtained from the second reception signal to evaluate the hardness of the tissue, and the pause period is a period from an end of the transmission of the second transmission signal to a start of a subsequent transmission of the first transmission signal.

In addition, it is preferable that the transmission circuit transmits a first transmission signal consisting of an excitation pulse as the ultrasound generating transmission signal to at least some of the plurality of ultrasound transducers, and generates the excitation ultrasonic waves from the plurality of ultrasound transducers and transmits the generated excitation ultrasonic waves to the tissue to excite the tissue to generate a shear wave, and then transmits a third transmission signal consisting of a detection pulse for detecting an acoustic velocity of the shear wave to at least some of the plurality of ultrasound transducers to generate a detection ultrasonic wave, and transmits the generated detection ultrasonic wave to the tissue in which the shear wave is generated, the reception circuit receives a third reception signal of the reflected wave of the detection ultrasonic wave from the tissue as the reception signal, the evaluation unit calculates the acoustic velocity of the shear wave based on the third reception signal to evaluate the hardness of the tissue, and the pause period is a period from an end of the transmission of the third transmission signal to a start of a subsequent transmission of the first transmission signal.

In addition, it is preferable that an ultrasound endoscope including an endoscope observation portion for acquiring an endoscope image, and the ultrasound observation portion is further provided.

In addition, to achieve the above object, an operation method of an ultrasound diagnostic system according to a second aspect of the present invention is an operation method of an ultrasound diagnostic system that acquires an ultrasound image and evaluates a hardness of a tissue of a diagnosis target using an acoustic radiation pressure, the ultrasound diagnostic system including an ultrasound observation portion, which has an ultrasound transducer array in which a plurality of ultrasound transducers are arranged, and an ultrasound processor device including a transmission circuit, which transmits an ultrasound generating transmission signal to the plurality of ultrasound transducers, a reception circuit, which outputs a reception signal of reflected waves received by the plurality of ultrasound transducers, and an evaluation unit, which evaluates the hardness of the tissue based on the reception signal, the operation method comprising a first signal generation step of controlling the transmission circuit to generate an ultrasound generating transmission signal consisting of driving pulses to be applied to the plurality of ultrasound transducers, to generate the ultrasonic waves from the plurality of ultrasound transducers; a first transmission step of transmitting the ultrasound generating transmission signal generated by the transmission circuit to the plurality of ultrasound transducers, applying the driving pulse to the plurality of ultrasound transducers to generate the ultrasonic wave including at least the excitation ultrasonic wave that generates the acoustic radiation pressure, and transmitting the generated ultrasonic wave to the tissue; an output step of receiving reflected waves from the tissue to which the ultrasonic wave has been delivered, via the plurality of ultrasound transducers, and outputting a reception signal based on the reflected waves received by the plurality of ultrasound transducers, from the reception circuit; an evaluation step of evaluating the hardness of the tissue via the evaluation unit based on the reception signal output from the reception circuit; a second signal generation step of controlling the transmission circuit to generate a polarization process transmission signal to be transmitted to the plurality of ultrasound transducers, to perform a polarization process on the plurality of ultrasound transducers that have transmitted the ultrasonic waves in a pause period of all transmissions of ultrasonic waves after the transmission of the ultrasonic wave; a setting step of, in the pause period after the transmission of the ultrasound generating transmission signal, which generates the ultrasonic wave including at least the excitation ultrasonic wave that generates the acoustic radiation pressure, setting a polarization process time for performing the polarization process within the pause period according to an acoustic output value generated in a case of the transmissions of the ultrasound generating transmission signal and the polarization process transmission signal; and a polarization step of transmitting the polarization process transmission signal from the transmission circuit to the plurality of ultrasound transducers that have transmitted at least the excitation ultrasonic waves, to perform the polarization process in the polarization process time.

Here, it is preferable that the setting step is a step of calculating the acoustic output value in the polarization process in response to an operation of a user on the tissue, and setting the polarization process time within the pause period such that the acoustic output value is equal to or less than a preset index value of acoustic output.

Further, it is preferable that the setting step is a step of calculating a level of depolarization of the plurality of ultrasound transducers generated by the transmission of the ultrasonic wave from a transmission time of the ultrasound generating transmission signal consisting of the driving pulse, calculating the acoustic output value in the polarization process from the calculated level of depolarization, and controlling the polarization process time within the pause period according to the calculated acoustic output value.

Further, it is preferable that the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to press and displace the tissue, the output step is a step of receiving a first reception signal based on the reflected wave from the tissue as the reception signal by the reception circuit, and outputting the first reception signal based on the reflected wave from the reception circuit, the evaluation step is a step of calculating the displacement of the tissue based on the ultrasound image obtained from the first reception signal to evaluate the hardness of the tissue via the evaluation unit, and the pause period is a period from an end of the transmission of the first transmission signal to a start of a subsequent transmission of the first transmission signal.

Further, it is preferable that the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to press and displace the tissue, the operation method further includes a third signal generation step of controlling the transmission circuit to generate a second transmission signal consisting of a detection pulse for detecting the displacement of the tissue after the tissue is displaced, and a second transmission step of transmitting the second transmission signal consisting of the detection pulse from the transmission circuit to the plurality of ultrasound transducers to generate a detection ultrasonic wave, and transmitting the generated detection ultrasonic wave to the tissue, the output step is a step of receiving a second reception signal based on the reflected wave of the detection ultrasonic wave from the tissue as the reception signal by the reception circuit, the evaluation step is a step of calculating the displacement of the tissue based on the ultrasound image obtained from the second reception signal to evaluate the hardness of the tissue via the evaluation unit, and the pause period is a period from an end of the transmission of the second transmission signal to a start of a subsequent transmission of the first transmission signal.

Further, it is preferable that the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to excite the tissue to generate a shear wave, the operation method further includes a fourth signal generation step of controlling the transmission circuit to generate a third transmission signal consisting of a detection pulse for detecting an acoustic velocity of the shear wave after the shear wave is generated, and a third transmission step of transmitting the third transmission signal consisting of the detection pulse from the transmission circuit to the plurality of ultrasound transducers to generate a detection ultrasonic wave, and transmitting the generated detection ultrasonic wave to the tissue in which the shear wave is generated, the output step is a step of receiving a third reception signal of the reflected wave of the detection ultrasonic wave from the tissue as the reception signal by the reception circuit, the evaluation step is a step of calculating the acoustic velocity of the shear wave based on the third reception signal to evaluate the hardness of the tissue via the evaluation unit, and the pause period is a period from an end of the transmission of the third transmission signal to a start of a subsequent transmission of the first transmission signal.

According to the present invention, in a case of performing ultrasonic elastography for examining a state such as a hardness of a tissue of an observation target part, in a pause period after a transmission of an ultrasound generating transmission signal, the ultrasound generating transmission signal consisting of an excitation pulse capable of generating an ultrasonic wave including an excitation ultrasonic wave that generates an acoustic radiation pressure, a polarization process of an ultrasound transducer can be performed by using an existing transmission circuit that has transmitted the transmission signal, and examination of the observation target part can be continued while maintaining performance without degradation in workflow.

According to the present invention, it is possible to appropriately set a polarization process time according to an acoustic output value generated in a case of transmitting a transmission signal for generating an ultrasonic wave and a transmission signal for performing a polarization process in a pause period, and it is possible to appropriately perform the polarization process on an ultrasound transducer in the set polarization process time.

According to the present invention, since the reception sensitivities of the plurality of ultrasound transducers can always be kept satisfactory without reducing the image quality of the ultrasound image, a high-quality ultrasound image can always be acquired without affecting the image quality of the ultrasound image.

In addition, according to the present invention, the polarization process of a plurality of ultrasound transducers is performed using the existing transmission circuit for transmitting the transmission signal to the ultrasound transducers of the ultrasound endoscope. Therefore, it is possible to perform the polarization process of the ultrasound transducers without significantly changing the existing circuit configuration and without causing an increase in the circuit size.

According to the present invention, even in a case where a single crystal transducer is adopted, it is possible to provide an ultrasound diagnostic system having a highly sensitive ultrasound endoscope capable of performing repolarization with a waveform optimal for the polarization and to provide an operation method of an ultrasound diagnostic system capable of performing repolarization with respect to polarization of the single crystal transducer with an optimal waveform in the highly sensitive ultrasound endoscope.

BRIEF DESCRIPTION OF THE DRAWINGS

FIG. 4 is a block diagram showing the configuration of an ultrasound processor device shown in FIG. 1.

FIG. 5 is a time chart showing a transmission period of a push pulse, a track pulse, and a polarization driving pulse transmitted from the transmission circuit shown in FIG. 4.

FIG. 6A is a graph showing an example of a driving waveform of a polarization driving pulse transmitted from a transmission circuit shown in FIG. 4.

FIG. 6B is a graph showing the relationship between the frequency and the sensitivity of the driving waveform of the polarization driving pulse shown in FIG. 6A.

FIG. 11 is a flowchart showing a procedure of an image generation step of the diagnosis step shown in FIG. 9.

DESCRIPTION OF THE PREFERRED EMBODIMENTS

An ultrasound diagnostic system according to an embodiment of the present invention will be described in detail below based on preferred embodiments shown in the accompanying diagrams.

The present embodiment is a representative embodiment of the present invention, but is merely an example and does not limit the present invention.

In addition, in the present specification, a numerical range represented using "to" means a range including numerical values described before and after the preposition "to" as a lower limit value and an upper limit value.

<<Outline of Ultrasound Diagnostic System>>

Figure 1:
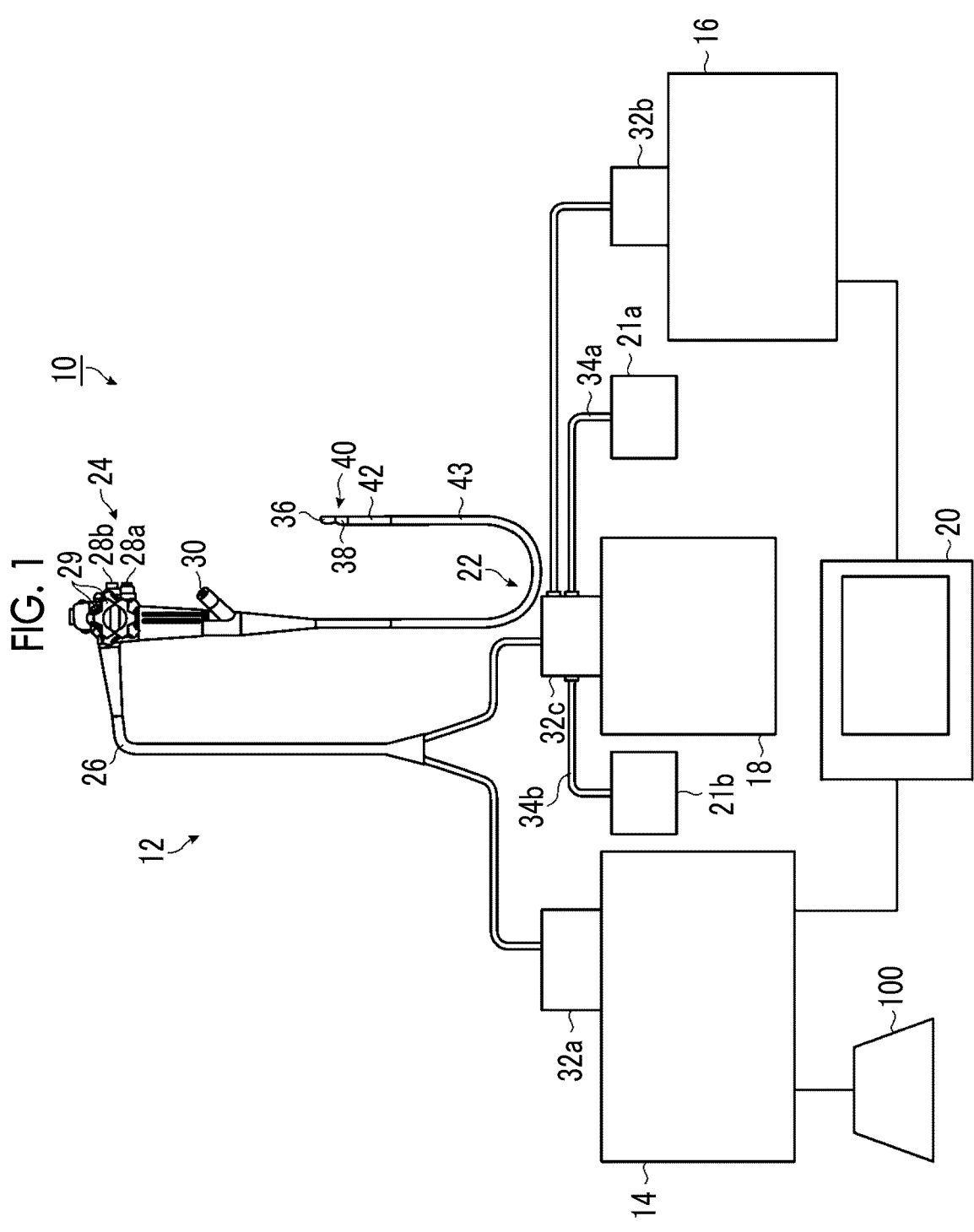
FIG. 1 is a diagram showing the schematic configuration of an ultrasound diagnostic system according to an embodiment of the present invention.

The outline of an ultrasound diagnostic system 10 according to the present embodiment will be described with reference to FIG. 1. FIG. 1 is a diagram showing the schematic configuration of the ultrasound diagnostic system 10.

The ultrasound diagnostic system 10 is used to acquire an ultrasound image or to evaluate a state of an observation target part in a body of a patient as a subject, particularly a hardness of a tissue, to perform diagnosis (hereinafter, also referred to as ultrasound diagnosis) using ultrasonic waves. The ultrasound diagnostic system 10 particularly performs evaluation of the hardness of the tissue of the observation target part (hereinafter, also referred to as diagnosis target) using an acoustic radiation pressure, and can perform ultrasonic elastography for the ultrasound diagnosis of the state of the observation target part and presence or absence of an abnormality by evaluating a hardness of the observation target part. The ultrasonic elastography is roughly classified into strain elastography for observing a strain of the tissue of the observation target part and shear wave elastography for measuring a propagation velocity of a shear wave of the tissue of the observation target part. However, in the present invention, it is possible to perform both the strain elastography and the shear wave elastography.

Here, the observation target part is a part that is difficult to examine from the body surface side of the patient, for example, a gallbladder or a pancreas. With the use of the ultrasound diagnostic system 10, it is possible to perform ultrasound diagnosis of a state of the observation target part and the presence or absence of an abnormality by way of digestive tracts, such as esophagus, stomach, duodenum, small intestine, and large intestine, which are body cavities of the patient.

Hereinafter, the ultrasound diagnostic system 10 will be described as having a function of performing the ultrasound diagnosis and a function of acquiring an endoscope image. However, in the present invention, the ultrasound diagnostic system 10 may have only a function of performing the ultrasound diagnosis and may perform only the ultrasound diagnosis. That is, the ultrasound diagnostic system 10 according to the embodiment of the invention may be an ultrasound diagnostic system that does not need to have an ultrasound endoscope 12 comprising an ultrasound observation portion 36 and an endoscope observation portion 38, which will be described later, that can perform ultrasonic elastography without having the endoscope observation portion 38 and a light source device 18 required for acquiring an endoscope image, and components required for only endoscope observation, and that has the ultrasound observation portion 36 for acquiring the ultrasound image and components required for only ultrasound observation.

The ultrasound diagnostic system 10 acquires an ultrasound image and an endoscope image, and as shown in FIG. 1, has the ultrasound endoscope 12, an ultrasound processor device 14, the endoscope processor device 16, the light source device 18, a monitor 20, a water supply tank 21a, a suction pump 21b, and a console 100.

Figure 2:
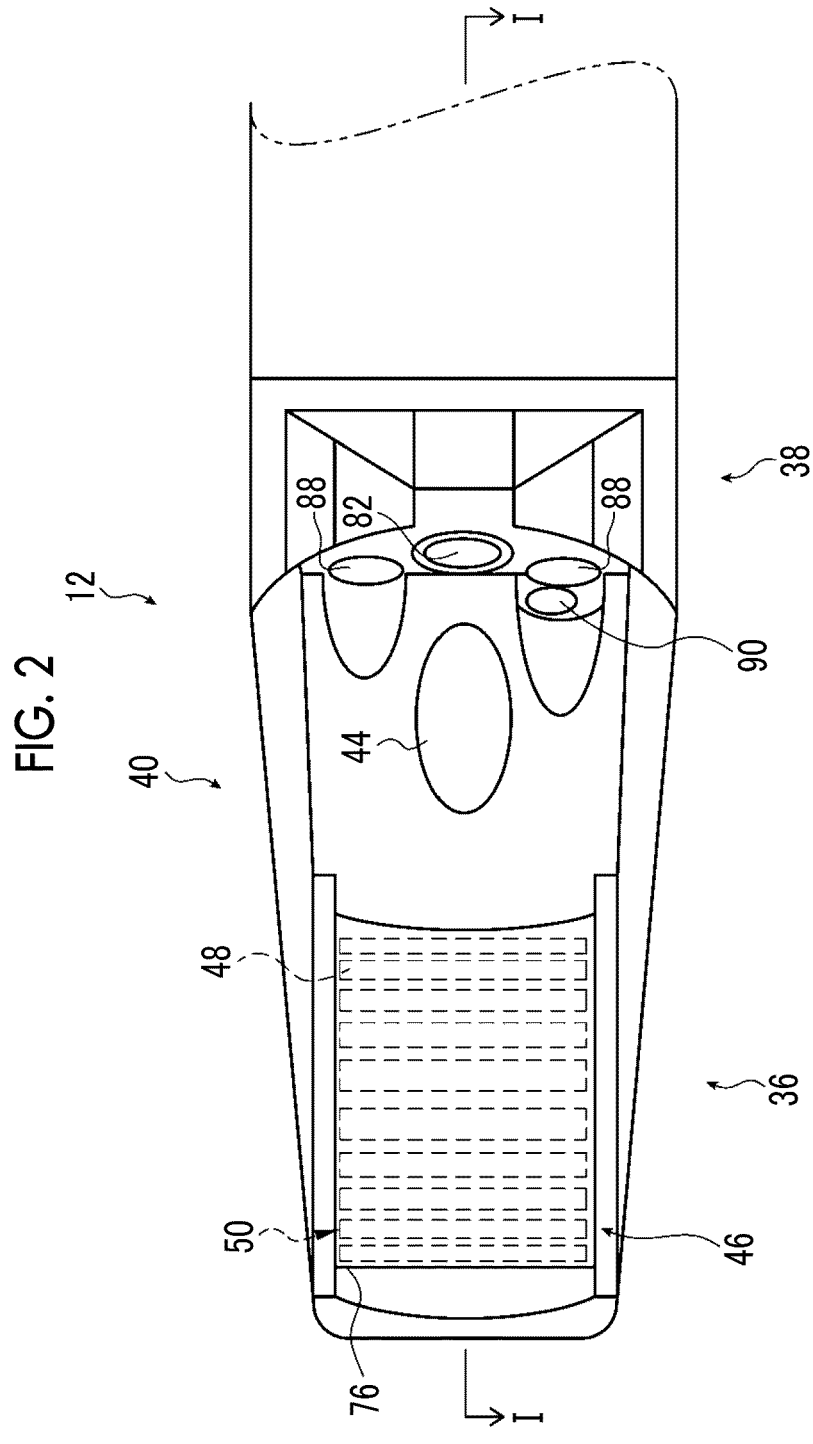
FIG. 2 is a plan view showing a distal end portion of an insertion part of an ultrasound endoscope and its periphery shown in FIG. 1.
Figure 3:
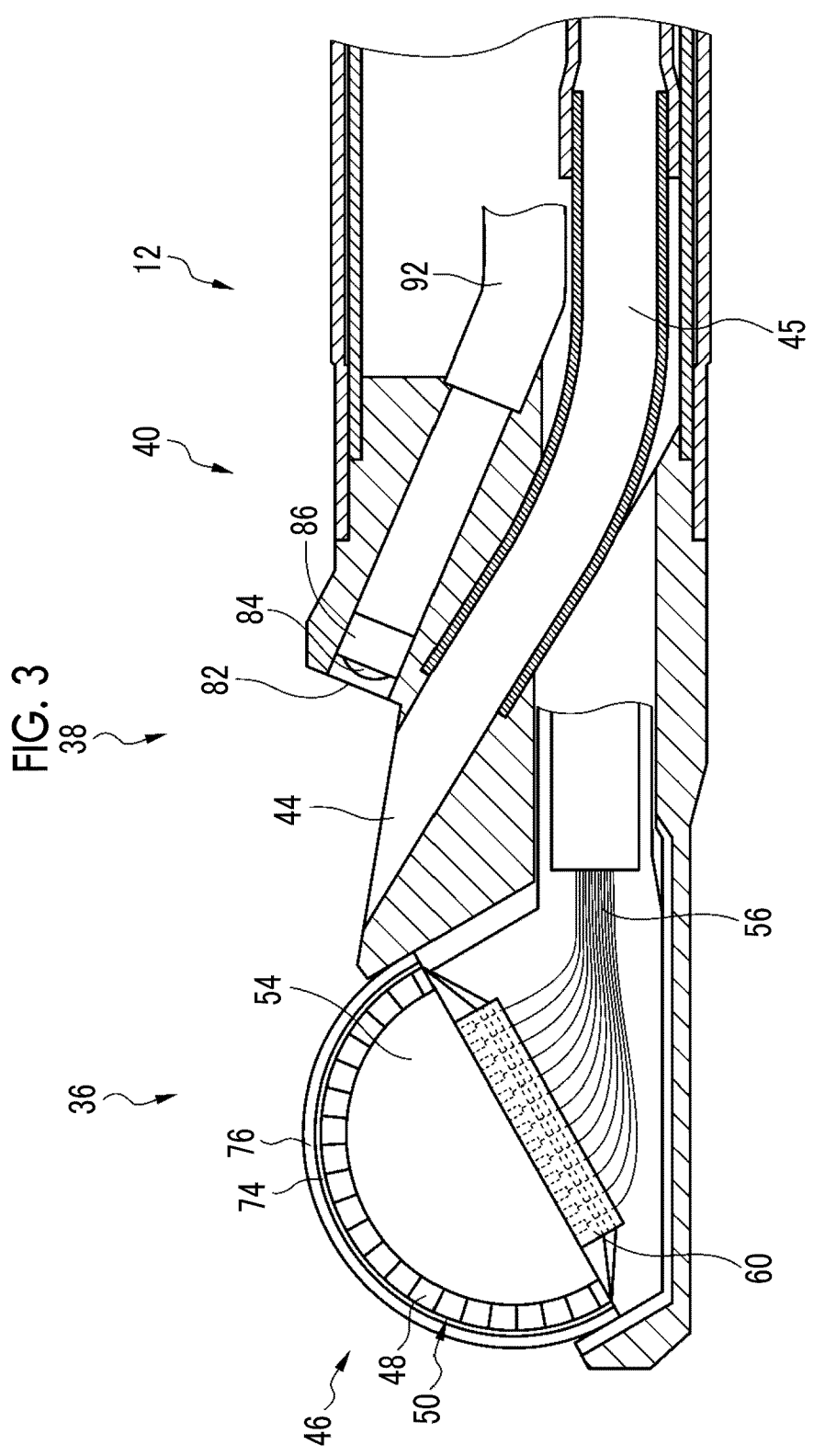
FIG. 3 is a diagram showing a cross section of the distal end portion of the insertion part of the ultrasound endoscope shown in FIG. 2 taken along line I-I in FIG. 2.

The ultrasound endoscope 12 is an endoscope, and comprises an insertion part 22 to be inserted into the body cavity of a patient, an operating part 24 operated by an operator (user), such as a doctor or a technician, and an ultrasound transducer unit 46 attached to a distal end portion 40 of the insertion part 22 (refer to FIGS. 2 and 3). By the function of the ultrasound endoscope 12, the operator can acquire an endoscope image of a body cavity inner wall of the patient and an ultrasound image of the observation target part.

Here, the "endoscope image" is an image that is obtained by imaging the body cavity inner wall of the patient using an optical method. Furthermore, the "ultrasound image" is an image that is obtained by receiving reflected waves (echoes) of ultrasonic waves transmitted from the inside of the body cavity of the patient toward the observation target part and imaging reception signals.

The ultrasound endoscope 12 will be described below in detail.

The ultrasound processor device 14 is connected to the ultrasound endoscope 12 through a universal cord 26 and an ultrasound connector 32a provided at an end portion of the universal cord 26. The ultrasound processor device 14 controls the ultrasound transducer unit 46 of the ultrasound endoscope 12 to transmit an ultrasonic wave such as an excitation ultrasonic wave that generates an acoustic radiation pressure for exciting a tissue of a diagnosis target, and as necessary, a detection ultrasonic wave for detecting a strain of the tissue or a shear wave generated in the tissue. In addition, the ultrasound processor device 14 generates an ultrasound image by imaging the reception signal in a case where the reflected wave (echo) of the transmitted ultrasonic wave is received by the ultrasound transducer unit 46.

The ultrasound processor device 14 will be described in detail later.

The endoscope processor device 16 is connected to the ultrasound endoscope 12 through the universal cord 26 and an endoscope connector 32b provided at an end portion of the universal cord 26. The endoscope processor device 16 generates an endoscope image by acquiring image data of an observation target adjacent part imaged by the ultrasound endoscope 12 (more specifically, a solid-state imaging element 86 to be described later) and performing predetermined image processing on the acquired image data.

Here, the "observation target adjacent part" is a portion that is at a position adjacent to the observation target part in the body cavity inner wall of the patient.

In the present embodiment, the ultrasound processor device 14 and the endoscope processor device 16 are formed by two devices (computers) provided separately. However, the present invention is not limited thereto, and both the ultrasound processor device 14 and the endoscope processor device 16 may be formed by one device.

The light source device 18 is connected to the ultrasound endoscope 12 through the universal cord 26 and a light source connector 32c provided at the end portion of the universal cord 26. The light source device 18 emits white light or specific wavelength light formed of three primary color light components of red light, green light, and blue light in a case of imaging the observation target adjacent part using the ultrasound endoscope 12. The light emitted from the light source device 18 propagates through the ultrasound endoscope 12 through a light guide (not shown) included in the universal cord 26, and is emitted from the ultrasound endoscope 12 (more specifically, an illumination window 88 to be described later). As a result, the observation target adjacent part is illuminated with the light from the light source device 18.

The monitor 20 is connected to the ultrasound processor device 14 and the endoscope processor device 16, and displays an ultrasound image generated by the ultrasound processor device 14 and an endoscope image generated by the endoscope processor device 16. As a display method of the ultrasound image and the endoscope image, either one of the images may be switched and displayed on the monitor 20, or both the images may be displayed at the same time. Display modes of the ultrasound image and the endoscope image will be described later.

In the present embodiment, although the ultrasound image and the endoscope image are displayed on one monitor 20, a monitor for ultrasound image display and a monitor for endoscope image display may be provided separately. In addition, the ultrasound image and the endoscope image may be displayed in a display form other than the monitor 20. For example, the ultrasound image and the endoscope image may be displayed on a display of a terminal carried by the operator.

The console 100 is a device provided for the operator to input information necessary for ultrasound diagnosis or for the operator to instruct the ultrasound processor device 14 to start ultrasound diagnosis. The console 100 is configured to include, for example, a keyboard, a mouse, a trackball, a touch pad, and a touch panel. In a case where the console 100 is operated, a CPU (control circuit) 152 (refer to FIG. 4) of the ultrasound processor device 14 controls each unit of the device (for example, a reception circuit 142 and a transmission circuit 144 to be described later) according to the operation content.

Specifically, the operator inputs examination information (for example, examination order information including a date, an order number, and the like, patient information including a patient ID, a patient name, and the like, and information on an examination content and an examination target part) through the console 100 before starting the ultrasound diagnosis. In a case where the operator gives an instruction to start the ultrasound diagnosis through the console 100 after the input of the examination information is completed, the CPU 152 of the ultrasound processor device 14 controls each unit of the ultrasound processor device 14 so that the ultrasound diagnosis is performed based on the input examination information.

Furthermore, the operator can set various control parameters through the console 100 in executing ultrasound diagnosis. As the control parameters, for example, a selection result of a live mode and a freeze mode, a set value of a display depth (depth), a selection result of an ultrasound image generation mode, and the like are exemplified.

Here, the "live mode" is a mode where ultrasound images (moving image) obtained at a predetermined frame rate are displayed successively (displayed in real time). The "freeze mode" is a mode in which an image (still image) of one frame of an ultrasound image (moving image) generated in the past is read out from a cine memory 150 to be described later and displayed.

There are a plurality of ultrasound image generation modes that can be selected in the present embodiment. Specifically, there are a brightness (B) mode, a color flow (CF) mode, and a pulse wave (PW) mode. The B mode is a mode in which a tomographic image is displayed by converting the amplitude of the ultrasound echo into a brightness. The CF mode is a mode where an average blood flow speed, flow fluctuation, intensity of a flow signal, flow power, or the like are mapped to various colors and superimposedly displayed on a B mode image. The PW mode is a mode in which the speed (for example, speed of blood flow) of the ultrasound echo source detected based on the transmission and reception of the pulse wave is displayed.

The above-described ultrasound image generation modes are merely an example, and modes other than the above-described three kinds of modes, for example, an amplitude (A) mode, a motion (M) mode, and a contrast mode may be further included or a mode in which a Doppler image is obtained may be included.

As described above, in the present embodiment, it goes without saying that the operator can select the ultrasonic elastography on the console 100 as examination for the ultrasound diagnosis.

<<Configuration of Ultrasound Endoscope 12>>

Next, the configuration of the ultrasound endoscope 12 will be described with reference to FIG. 1 described above, and FIGS. 2 to 4. FIG. 2 is an enlarged plan view showing a distal end portion of an insertion part 22 of an ultrasound endoscope 12 and the periphery thereof. FIG. 3 is a cross-sectional view showing a cross section of the distal end portion 40 of the insertion part 22 of the ultrasound endoscope 12 taken along line I-I in FIG. 2.

As described above, the ultrasound endoscope 12 has the insertion part 22 and the operating part 24. As shown in FIG. 1, the insertion part 22 comprises the distal end portion 40, a bendable portion 42, and a soft portion 43 in order from the distal end side (free end side). As shown in FIG. 2, the ultrasound observation portion 36 and the endoscope observation portion 38 are provided in the distal end portion 40. As shown in FIG. 3, the ultrasound transducer unit 46 comprising a plurality of ultrasound transducers 48 is arranged in the ultrasound observation portion 36.

Furthermore, as shown in FIG. 2, a treatment tool outlet port 44 is provided in the distal end portion 40. The treatment tool outlet port 44 serves as an outlet of a treatment tool (not shown), such as forceps, an puncture needle, or a high frequency scalpel. In addition, the treatment tool outlet port 44 serves as a suction port in the case of sucking aspirates, such as blood and body waste.

The bendable portion 42 is a portion consecutively provided on a proximal end side (a side opposite to a side on which the ultrasound transducer unit 46 is provided) than the distal end portion 40, and is freely bent. The soft portion 43 is a portion connecting the bendable portion 42 and the operating part 24 to each other, has flexibility, and is provided so as to extend in an elongated state.

A plurality of pipe lines for air and water supply and a plurality of pipe lines for suction are formed inside each of the insertion part 22 and the operating part 24. In addition, a treatment tool channel 45 whose one end communicates with the treatment tool outlet port 44 is formed in each of the insertion part 22 and the operating part 24.

Next, the ultrasound observation portion 36, the endoscope observation portion 38, the water supply tank 21a, the suction pump 21b, and the operating part 24 among the components of the ultrasound endoscope 12 will be described in detail.

(Ultrasound Observation Portion)

The ultrasound observation portion 36 is a portion that is provided to acquire an ultrasound image, and is arranged on the distal end side in the distal end portion 40 of the insertion part 22. As shown in FIG. 3, the ultrasound observation portion 36 comprises the ultrasound transducer unit 46, a plurality of coaxial cables 56, and a flexible printed circuit (FPC) 60.

The ultrasound transducer unit 46 corresponds to an ultrasound probe (probe), transmits ultrasonic waves using an ultrasound transducer array 50, in which a plurality of ultrasound transducers 48 described below are arranged, inside a body cavity of a patient, receives reflected waves (echoes) of the ultrasonic waves reflected by the observation target part, and outputs reception signals. The ultrasound transducer unit 46 according to the present embodiment is a convex type, and transmits an ultrasonic wave radially (in an arc shape). However, the type (model) of the ultrasound transducer unit 46 is not particularly limited, and other types may be used as long as it is possible to transmit and receive ultrasonic waves. For example, a sector type, a linear type, and a radial type may be used.

As shown in FIG. 3, the ultrasound transducer unit 46 is formed by laminating a backing material layer 54, the ultrasound transducer array 50, an acoustic matching layer 74, and an acoustic lens 76.

The ultrasound transducer array 50 has a plurality of ultrasound transducers 48 arranged in a one-dimensional array. More specifically, the ultrasound transducer array 50 is formed by arranging N (for example, N=128) ultrasound transducers 48 at equal intervals in a convex bending shape along the axial direction of the distal end portion 40 (longitudinal axis direction of the insertion part 22). The ultrasound transducer array 50 may be one in which a plurality of ultrasound transducers 48 are arranged in a two-dimensional array.

Each of the N ultrasound transducers 48 is formed by arranging electrodes on both surfaces of a single crystal transducer that is a piezoelectric element. As the single crystal transducer, any of quartz, lithium niobate, lead magnesium niobate (PMN), lead magnesium niobate-lead titanate (PMN-PT), lead zinc niobate (PZN), lead zinc niobate-lead titanate (PZN-PT), lead indium niobate (PIN), lead titanate (PT), lithium tantalate, langasite, and zinc oxide can be used.

The electrodes have an individual electrode (not shown) individually provided for each of a plurality of ultrasound transducers 48 and a transducer ground (not shown) common to a plurality of ultrasound transducers 48. In addition, the electrodes are electrically connected to the ultrasound processor device 14 through the coaxial cable 56 and the FPC 60.

The ultrasound transducer 48 according to the present embodiment needs to be driven (vibrated) at a relatively high frequency of 7 MHz to 8 MHz level in order to acquire an ultrasound image in the body cavity of the patient. For this reason, the thickness of the piezoelectric element forming the ultrasound transducer 48 is designed to be relatively small. For example, the thickness of the piezoelectric element forming the ultrasound transducer 48 is 75 μm to 125 μm, preferably 90 μm to 110 μm.

A diagnostic driving pulse that has a pulsed driving voltage is supplied from the ultrasound processor device 14 to each ultrasound transducer 48, as an input signal (transmission signal), through the coaxial cable 56. In a case where the driving voltage is applied to the electrodes of the ultrasound transducer 48, the piezoelectric element expands and contracts to drive (vibrate) the ultrasound transducer 48. As a result, a pulsed ultrasonic wave is output from the ultrasound transducer 48. In this case, the amplitude of the ultrasonic wave output from the ultrasound transducer 48 has magnitude according to intensity (output intensity) in a case where the ultrasound transducer 48 outputs the ultrasonic wave. Here, the output intensity is defined as the magnitude of the sound pressure of the ultrasonic wave output from the ultrasound transducer 48.

In addition, the ultrasound transducer 48 according to the present embodiment not only receives an excitation pulse such as a push pulse of a strong ultrasound output for performing ultrasonic elastography as a driving pulse to generate an excitation ultrasonic wave, but also receives a detection pulse such as a track pulse for detecting a shear elastic wave, that is, a shear wave, which is a transverse wave generated by a displacement (strain) of a tissue of an observation target part by the excitation ultrasonic wave or by excitation of the tissue of the observation target part by the excitation ultrasonic wave, to generate a detection ultrasonic wave.

Each ultrasound transducer 48 vibrates (is driven) with reception of a reflected wave (echo) of the ultrasonic wave, and the piezoelectric element of each ultrasound transducer 48 generates an electric signal. In a case where the ultrasonic elastography is performed, the reflected wave received by each ultrasound transducer 48 may be a reflected wave directly reflected from the tissue of the observation target part that is pressed and displaced by receiving the excitation ultrasonic wave generated by the excitation pulse, may be a reflected wave of a detection ultrasonic wave generated by the detection pulse for detecting the displacement (strain) of the tissue of the observation target part that is pressed and displaced by receiving the excitation ultrasonic wave, or may be a reflected wave of a detection ultrasonic wave for detecting a shear wave generated in the tissue of the observation target part that is excited by receiving the excitation ultrasonic wave.

The electric signal generated by each ultrasound transducer 48 is output from each ultrasound transducer 48 to the ultrasound processor device 14 as a reception signal of the ultrasonic wave. In this case, the magnitude (voltage value) of the electric signal output from the ultrasound transducer 48 has a magnitude corresponding to the reception sensitivity in a case where the ultrasound transducer 48 receives the ultrasonic wave. Here, the reception sensitivity is defined as a ratio of the amplitude of the electric signal, which is output from the ultrasound transducer 48 in response to reception of the ultrasonic wave, to the amplitude of the ultrasonic wave transmitted by the ultrasound transducer 48.

In the present embodiment, the N ultrasound transducers 48 are driven sequentially by an electronic switch, such as a multiplexer 140 (see FIG. 4), scanning with ultrasonic waves is performed in a scanning range along a curved surface on which the ultrasound transducer array 50 is arranged, for example, a range of about several tens of mm from the center of curvature of the curved surface. More specifically, in the case of acquiring a B mode image (tomographic image) as an ultrasound image, a driving voltage is supplied to m (for example, m=N/2) ultrasound transducers 48 (hereinafter, referred to as driving target transducers) arranged in series, among the N ultrasound transducers 48, by opening channel selection of the multiplexer 140. With this, the m driving target transducers are driven, and an ultrasonic wave is output from each driving target transducer of the opening channel. The ultrasonic waves output from the m driving target transducers are immediately composed, and the composite wave (ultrasound beam) is transmitted toward the observation target part. Thereafter, each of the m driving target transducers receives an ultrasonic wave (echo) reflected at the observation target part, and outputs an electric signal (reception signal) corresponding to the reception sensitivity at that point in time.

Then, the above-described series of steps (that is, the supply of the driving voltage, the transmission and reception of the ultrasonic waves, and the output of the electric signal) are repeatedly performed while shifting the positions of the driving target transducers among the N ultrasound transducers 48 one by one (one ultrasound transducer 48 at a time). Specifically, the above-described series of steps are started from m driving target transducers on both sides of the ultrasound transducer 48 located at one end among the N ultrasound transducers 48. Then, the above-described series of steps are repeated each time the positions of the driving target transducers are shifted due to switching of the opening channel by the multiplexer 140. Finally, the above-described series of steps are repeatedly performed a total of N times up to m driving target transducers on both sides of the ultrasound transducer 48 located at the other end among the N ultrasound transducers 48.

The backing material layer 54 supports each ultrasound transducer 48 of the ultrasound transducer array 50 from a rear surface side. Furthermore, the backing material layer 54 has a function of attenuating ultrasonic waves propagating to the backing material layer 54 side among ultrasonic waves emitted from the ultrasound transducers 48 or ultrasonic waves (echoes) reflected by the observation target part. The backing material is a material having rigidity, such as hard rubber, and an ultrasound attenuating material (ferrite, ceramics, and the like) is added as necessary.

The acoustic matching layer 74 is superimposed on the ultrasound transducer array 50, and is provided for acoustic impedance matching between the body of the patient and the ultrasound transducer 48. The acoustic matching layer 74 is provided, whereby it is possible to increase the transmittance of the ultrasonic wave. As a material of the acoustic matching layer 74, various organic materials of which a value of acoustic impedance is closer to that of the body of the patient than the piezoelectric element of the ultrasound transducer 48 can be used. Specific examples of the material of the acoustic matching layer 74 include epoxy resin, silicone rubber, polyimide, polyethylene, and the like.

The acoustic lens 76 superimposed on the acoustic matching layer 74 converges ultrasonic waves emitted from the ultrasound transducer array 50 toward the observation target part. The acoustic lens 76 is formed of, for example, silicon resin (millable silicone rubber (HTV rubber), liquid silicone rubber (RTV rubber), and the like), butadiene resin, and polyurethane resin, and powders of titanium oxide, alumina, silica, and the like are mixed as necessary.

The FPC 60 is electrically connected to the electrodes of each ultrasound transducer 48. Each of the plurality of coaxial cables 56 is wired to the FPC 60 at one end thereof. Then, in a case where the ultrasound endoscope 12 is connected to the ultrasound processor device 14 through the ultrasound connector 32a, each of the plurality of coaxial cables 56 is electrically connected to the ultrasound processor device 14 at the other end (side opposite to the FPC 60 side).

Figure 4:
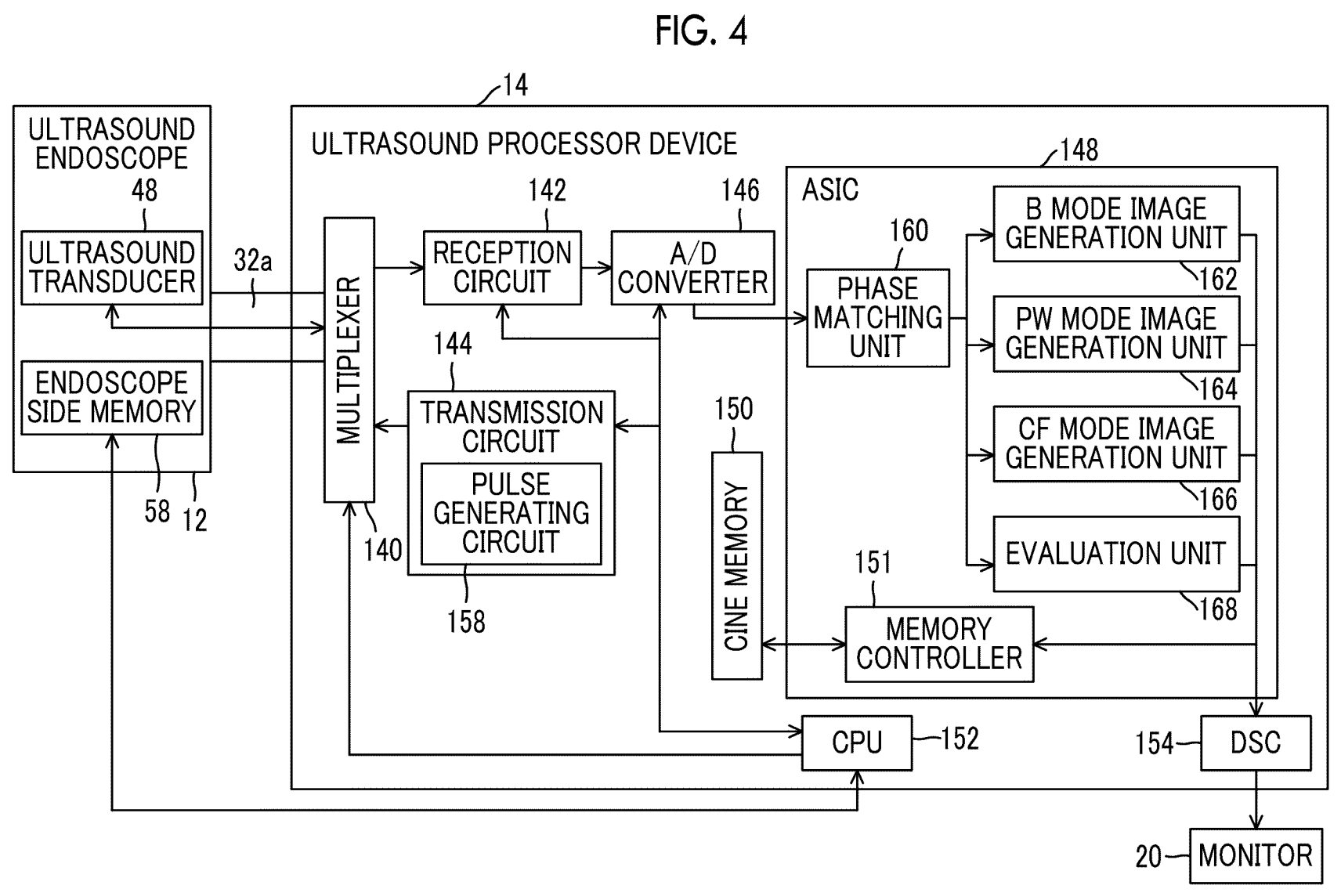

Further, in the present embodiment, the ultrasound endoscope 12 comprises an endoscope side memory 58 (refer to FIG. 4). The endoscope side memory 58 may store driving times of the plurality of ultrasound transducers 48 in a case of ultrasound diagnosis. Strictly speaking, the endoscope side memory 58 may store the cumulative driving time of the driving target transducer among the plurality of ultrasound transducers 48. The ultrasound transducer 48 of which the cumulative driving time exceeds a predetermined value may be excluded from the driving target transducer, and the excluded ultrasound transducer 48 may be subjected to the polarization process.

In the present embodiment, an execution period of ultrasound diagnosis, that is, a period from the start of acquisition of an ultrasound image (moving image) to the end thereof (more specifically, a time during which ultrasound diagnosis is performed in the live mode), is set as the cumulative driving time. However, the present invention is not limited thereto, and the time for which the driving voltage is supplied to the driving target transducer may be set as the cumulative driving time.

In a state in which the ultrasound endoscope 12 is connected to the ultrasound processor device 14, the CPU 152 of the ultrasound processor device 14 can also access the endoscope side memory 58 to read the cumulative driving time stored in the endoscope side memory 58. In addition, the CPU 152 of the ultrasound processor device 14 may rewrite the cumulative driving time stored in the endoscope side memory 58 to a default value, or may update the stored cumulative driving time to a new cumulative driving time in a case where the cumulative driving time changes with the execution of ultrasound diagnosis.

(Endoscope Observation Portion)

The endoscope observation portion 38 is a portion that is provided to acquire an endoscope image, and is arranged on a proximal end side than the ultrasound observation portion 36 in the distal end portion 40 of the insertion part 22. As shown in FIGS. 2 and 3, the endoscope observation portion 38 includes an observation window 82, an objective lens 84, the solid-state imaging element 86, the illumination window 88, a cleaning nozzle 90, a wiring cable 92, and the like.

The observation window 82 is attached in a state obliquely inclined with respect to the axial direction (the longitudinal axis direction of the insertion part 22) in the distal end portion 40 of the insertion part 22. Light incident through the observation window 82 and reflected at the observation target adjacent part is formed on the imaging surface of the solid-state imaging element 86 by the objective lens 84.

The solid-state imaging element 86 photoelectrically converts reflected light of the observation target adjacent part transmitted through the observation window 82 and the objective lens 84 and formed on the imaging surface, and outputs an imaging signal. As the solid-state imaging element 86, it is possible to use a charge coupled device (CCD), a complementary metal oxide semiconductor (CMOS), and the like. The captured image signal output from the solid-state imaging element 86 is transmitted to the endoscope processor device 16 by the universal cord 26 through the wiring cable 92 extending from the insertion part 22 to the operating part 24.

The illumination windows 88 are provided at both side positions of the observation window 82. An exit end of a light guide (not shown) is connected to the illumination window 88. The light guide extends from the insertion part 22 to the operating part 24, and its incidence end is connected to the light source device 18 connected through the universal cord 26. The illumination light emitted from the light source device 18 is transmitted through the light guide and is emitted from the illumination window 88 toward the observation target adjacent part.

The cleaning nozzle 90 is an ejection hole formed in the distal end portion 40 of the insertion part 22 in order to clean the surfaces of the observation window 82 and the illumination windows 88, and air or a cleaning liquid is ejected from the cleaning nozzle 90 toward the observation window 82 and the illumination windows 88. In the present embodiment, the cleaning liquid ejected from the cleaning nozzle 90 is water, in particular, degassed water. However, the cleaning liquid is not particularly limited, and other liquids, for example, normal water (water that is not degassed) may be used.

(Water Supply Tank and Suction Pump)

The water supply tank 21a is a tank that stores degassed water, and is connected to the light source connector 32c by an air/water supply tube 34a. Degassed water is used as a cleaning liquid ejected from the cleaning nozzle 90.

The suction pump 21b sucks aspirates (including degassed water supplied for cleaning) into the body cavity through the treatment tool outlet port 44. The suction pump 21b is connected to the light source connector 32c by a suction tube 34b. The ultrasound diagnostic system 10 may comprise an air supply pump that supplies air to a predetermined air supply destination, or the like.

Inside the insertion part 22 and the operating part 24, the treatment tool channel 45 and an air/water supply pipe line (not shown) are provided.

The treatment tool channel 45 communicates a treatment tool insertion port 30 and the treatment tool outlet port 44 provided in the operating part 24. Furthermore, the treatment tool channel 45 is connected to a suction button 28b provided in the operating part 24. The suction button 28b is connected to the suction pump 21b in addition to the treatment tool channel 45.

The air/water supply pipe line communicates with the cleaning nozzle 90 on one end side, and is connected to an air/water supply button 28a provided in the operating part 24 on the other end side. The air/water supply button 28a is connected to the water supply tank 21a in addition to the air/water supply pipe line.

(Operating Part)

The operating part 24 is a portion that is operated by the operator in a case of a start of ultrasound diagnosis, during diagnosis, in a case of an end of diagnosis, and the like, and has one end to which one end of the universal cord 26 is connected. As shown in FIG. 1, the operating part 24 has the air/water supply button 28a, the suction button 28b, a pair of angle knobs 29, and a treatment tool insertion port (forceps port) 30.

In a case where each of a pair of angle knobs 29 is moved rotationally, the bendable portion 42 is remotely operated to be bent and deformed. By this deformation operation, the distal end portion 40 of the insertion part 22 in which the ultrasound observation portion 36 and the endoscope observation portion 38 are provided can be directed in a desired direction.

The treatment tool insertion port 30 is a hole formed in order that the treatment tool (not shown), such as forceps, is inserted thereinto, and communicates with the treatment tool outlet port 44 through the treatment tool channel 45. The treatment tool inserted into the treatment tool insertion port 30 is introduced into the body cavity from the treatment tool outlet port 44 after passing through the treatment tool channel 45.

The air/water supply button 28a and the suction button 28b are two-stage switching type push buttons, and are operated to switch opening and closing of the pipe line provided inside each of the insertion part 22 and the operating part 24.

<<Configuration of Ultrasound Processor Device>>

The ultrasound processor device 14 makes the ultrasound transducer unit 46 transmit and receive ultrasonic waves and generates an ultrasound image by imaging reception signals output from the ultrasound transducers 48 (in detail, the driving target transducers) in a case of reception of the ultrasonic waves. In addition, the ultrasound processor device 14 displays the generated ultrasound image on the monitor 20.

Further, in the present embodiment, the ultrasound processor device 14 supplies a polarization voltage to a polarization target transducer, among the N ultrasound transducers 48, to polarize the polarization target transducer. By performing the polarization process, the depolarized ultrasound transducer 48 can be polarized again by repeating the ultrasound diagnosis. As a result, it is possible to restore the reception sensitivity of the ultrasound transducer 48 with respect to ultrasonic waves to a satisfactory level.

As shown in FIG. 4, the ultrasound processor device 14 has the multiplexer 140, the reception circuit 142, the transmission circuit 144, an A/D converter 146, an application specific integrated circuit (ASIC) 148, the cine memory 150, the central processing unit (CPU) 152, and a digital scan converter (DSC) 154.

The reception circuit 142 and the transmission circuit 144 are electrically connected to the ultrasound transducer array 50 of the ultrasound endoscope 12. The multiplexer 140 selects a maximum of m driving target transducers from the N ultrasound transducers 48, and opens their channels.

The transmission circuit 144 has a field programmable gate array (FPGA), a pulser (pulse generating circuit 158), a switch (SW), and the like, and is connected to the multiplexer 140 (MUX). Instead of the FPGA, an application specific integrated circuit (ASIC) may be used.

The transmission circuit 144 is a circuit that supplies a driving voltage for ultrasonic wave transmission to the driving target transducers selected by the multiplexer 140 in response to a control signal sent from the CPU 152 for transmission of ultrasonic waves from the ultrasound transducer unit 46. The driving voltage is a pulsed voltage signal (transmission signal), and is applied to the electrodes of the driving target transducers through the universal cord 26 and the coaxial cable 56.

The transmission circuit 144 has the pulse generating circuit 158 that generates a transmission signal based on the control signal. Under the control of the CPU 152, the transmission circuit 144 generates a transmission signal for driving a plurality of ultrasound transducers 48 to generate ultrasonic waves using the pulse generating circuit 158 and supplies the transmission signal to a plurality of ultrasound transducers 48.

In addition, under the control of the CPU 152, in the case of performing ultrasound diagnosis, the transmission circuit 144 generates an ultrasound generating transmission signal having a driving voltage for performing ultrasound diagnosis using the pulse generating circuit 158. Here, to perform the ultrasonic elastography, the pulse generating circuit 158 of the transmission circuit 144 needs to generate a first transmission signal consisting of an excitation pulse, that is, a push pulse that generates an excitation ultrasonic wave in the ultrasound transducer 48 as the ultrasound generating transmission signal. In addition, the pulse generating circuit 158 also needs to generate a second transmission signal consisting of a detection pulse for detecting the strain generated in the tissue of the diagnosis target by an excitation ultrasonic wave by the push pulse, or a third transmission signal consisting of a detection pulse for measuring a propagation velocity of a shear wave generated in the tissue of the diagnosis target by the excitation ultrasonic wave by the push pulse, as the ultrasound generating transmission signal for generating a detection ultrasonic wave in the ultrasound transducer 48.

In addition, under the control of the CPU 152, in a case where the polarization process is performed after only the excitation ultrasonic wave by the push pulse is transmitted to the tissue of the diagnosis target or after the excitation ultrasonic wave and the detection ultrasonic wave by the detection pulse are transmitted to the tissue of the diagnosis target, the polarization process transmission signal having the polarization voltage for performing the polarization process is generated using the same pulse generating circuit 158 as in a case where the ultrasound generating transmission signal is generated.

In a case where the first transmission signal consisting of the push pulse is transmitted to the ultrasound transducer 48, the excitation ultrasonic wave generated from the ultrasound transducer 48 is transmitted to the tissue of the diagnosis target to displace the tissue to generate a strain or to excite the tissue to generate a shear wave. In this case, the ultrasound transducer 48 receives a reflected wave (echo) from the tissue in which the strain has been generated with respect to the excitation ultrasonic wave, and generates a first reception signal.

Meanwhile, in a case where the second transmission signal and the third transmission signal consisting of the detection pulse are transmitted to the ultrasound transducer 48, the detection ultrasonic waves generated from the ultrasound transducers 48 are transmitted to the tissue in which a strain has been generated and the tissue in which a shear wave has been generated, respectively, and the ultrasound transducers 48 receives reflected waves (echoes) from the tissue in which the strain has been generated and reflected waves (echoes) corresponding to the shear wave from the tissue in which the shear wave has been generated with respect to the detection ultrasonic waves, respectively, to generate a second reception signal and a third reception signal.

The reception circuit 142 is a circuit that receives an electric signal output from the driving target transducer that has received an ultrasonic wave (echo), that is, a reception signal. The reception circuit 142 receives the first reception signal of the reflected wave of the excitation ultrasonic wave from the tissue in which a strain has been generated, the second reception signal of the reflected wave of the detection ultrasonic wave from the tissue in which the strain has been generated, or a third reception signal of the reflected wave of the detection ultrasonic wave from the tissue in which a shear wave has been generated, each of which is generated from the ultrasound transducer 48.

In addition, according to the control signal sent from the CPU 152, the reception circuit 142 amplifies the reception signal received from the ultrasound transducer 48 and transmits the amplified signal to the A/D converter 146. The A/D converter 146 is connected to the reception circuit 142, and converts the reception signal received from the reception circuit 142 from an analog signal to a digital signal and outputs the converted digital signal to the ASIC 148.

The ASIC 148 is connected to the A/D converter 146. As shown in FIG. 4, the ASIC 148 forms a phase matching unit 160, a B mode image generation unit 162, a PW mode image generation unit 164, a CF mode image generation unit 166, an evaluation unit 168, and a memory controller 151.

In the present embodiment, the above-described functions (specifically, the phase matching unit 160, the B mode image generation unit 162, the PW mode image generation unit 164, the CF mode image generation unit 166, the evaluation unit 168, and the memory controller 151) are realized by a hardware circuit, such as the ASIC 148. However, the present invention is not limited thereto. The above-described functions may be realized by making the central processing unit (CPU) and software (computer program) for executing various kinds of data processing cooperate with each other.

The phase matching unit 160 executes processing of giving a delay time to the reception signals (reception data) digitized by the A/D converter 146 and performing phasing addition (performing addition after matching the phases of the reception data). By the phasing addition processing, a sound ray signal with narrowed focus of the ultrasound echo is generated.

The B mode image generation unit 162, the PW mode image generation unit 164, and the CF mode image generation unit 166 generate an ultrasound image based on the electric signal (strictly speaking, a sound ray signal generated by phasing and adding the reception data) that is output from the driving target transducer among the plurality of ultrasound transducers 48 in a case where the ultrasound transducer unit 46 receives the ultrasonic wave (echo).

The B mode image generation unit 162 is an image generation unit that generates a B mode image as a tomographic image of the inside (the inside of the body cavity) of the patient. For the sequentially generated sound ray signals, the B mode image generation unit 162 corrects the attenuation due to the propagation distance according to the depth of the reflection position of the ultrasonic wave by sensitivity time gain control (STC). The B mode image generation unit 162 performs envelope detection processing and logarithm (Log) compression processing on the corrected sound ray signal, thereby generating a B mode image (image signal).

The PW mode image generation unit 164 is an image generation unit that generates an image indicating a speed of a blood flow in a predetermined direction. The PW mode image generation unit 164 extracts a frequency component by performing fast Fourier transform on a plurality of sound ray signals in the same direction among the sound ray signals sequentially generated by the phase matching unit 160. Thereafter, the PW mode image generation unit 164 calculates the speed of blood flow from the extracted frequency component, and generates a PW mode image (image signal) indicating the calculated speed of blood flow.

The CF mode image generation unit 166 is an image generation unit that generates an image indicating information regarding a blood flow in the predetermined direction. The CF mode image generation unit 166 generates an image signal indicating information regarding the blood flow by obtaining autocorrelation of a plurality of sound ray signals in the same direction among the sound ray signals sequentially generated by the phase matching unit 160. Thereafter, based on the image signal described above, the CF mode image generation unit 166 generates a CF mode image (image signal) as a color image in which the blood flow information is superimposed on the B mode image signal generated by the B mode image generation unit 162.

The evaluation unit 168 evaluates the hardness of the tissue of the diagnosis target based on the electric signal (strictly speaking, a sound ray signal generated by phasing and adding the reception data) that is output from the driving target transducer among the plurality of ultrasound transducers 48 in a case where the ultrasound transducer unit 46 receives the reflected wave (ultrasound echo).

The evaluation unit 168 calculates the displacement (strain) of the tissue of the diagnosis target to evaluate the hardness of the tissue based on the obtained ultrasound image from the first reception signal in a case where the reception circuit 142 receives the first reception signal, or from the second reception signal in a case where the reception circuit 142 receives the second reception signal, the obtained ultrasound image being, for example, the B mode ultrasound image generated by the B mode image generation unit 162. In addition, in a case where the reception circuit 142 receives the third reception signal, the evaluation unit 168 calculates an acoustic velocity of the shear wave generated in the tissue of the diagnosis target to evaluate the hardness of the tissue based on the third reception signal.

These hardness evaluations can be performed with reference to the following URL.

https://www.jstage.jst.go.jp/article/mit/32/2/32_75/_pdf

The memory controller 151 stores the image signal generated by the B mode image generation unit 162, the PW mode image generation unit 164, or the CF mode image generation unit 166 in the cine memory 150.

The DSC 154 is connected to the ASIC 148, converts (raster conversion) the signal of the image generated by the B mode image generation unit 162, the PW mode image generation unit 164, or the CF mode image generation unit 166 into an image signal compliant with a normal television signal scanning system, executes various kinds of necessary image processing, such as gradation processing, on the image signal, and then, outputs the image signal to the monitor 20.

The cine memory 150 has a capacity for accumulating an image signal for one frame or image signals for several frames. An image signal generated by the ASIC 148 is output to the DSC 154, and is stored in the cine memory 150 by the memory controller 151. In a freeze mode, the memory controller 151 reads out the image signal stored in the cine memory 150 and outputs the image signal to the DSC 154. As a result, an ultrasound image (still image) based on the image signal read from the cine memory 150 is displayed on the monitor 20.

The CPU 152 functions as a control unit (control circuit) that controls each unit of the ultrasound processor device 14, is connected to the reception circuit 142, the transmission circuit 144, the A/D converter 146, and the ASIC 148, and controls such circuits. Specifically, the CPU 152 is connected to the console 100, and controls each unit of the ultrasound processor device 14 according to examination information, control parameters, and the like input through the console 100.

The CPU 152 automatically recognizes the ultrasound endoscope 12 based on a method, such as Plug and Play (PnP), in a case where the ultrasound endoscope 12 is connected to the ultrasound processor device 14 through the ultrasound connector 32a. Thereafter, the CPU 152 can also access the endoscope side memory 58 of the ultrasound endoscope 12 to read the cumulative driving time stored in the endoscope side memory 58.

In addition, the CPU 152 may access the endoscope side memory 58 in a case of the end of the ultrasound diagnosis, and may update the cumulative driving time stored in the endoscope side memory 58 to a value obtained by adding the time required for the ultrasound diagnosis performed immediately before to the cumulative driving time stored in the endoscope side memory 58.

In the present embodiment, the cumulative driving time is stored on the ultrasound endoscope 12. However, the present invention is not limited thereto, and the cumulative driving time may be stored on the ultrasound processor device 14 side for each ultrasound endoscope 12.

Meanwhile, in the related art, as described above, during the execution period of the ultrasound diagnosis, in a case where the excitation pulse (push pulse) is generated in the pulse generating circuit 158 and the generated excitation pulses are supplied from the transmission circuit 144 to the plurality of ultrasound transducers 48 of the ultrasound transducer array 50 to generate strong excitation ultrasonic waves in a short period of time to output the generated excitation ultrasonic waves to the tissue of the diagnosis target, an attenuated spatial peak temporal average intensity (hereinafter, also simply referred to as temporal average intensity) Ispta.$\alpha$ is increased, or the temporal average intensity Ispta.$\alpha$ exceeds or may exceed the limit value of 720 mW/cm$^2$ of US FDA. Accordingly, after strong excitation ultrasonic waves are output in a short period of time, a pause period (freeze period) is provided.

In addition, as described above, in a case where the push pulses are supplied to the plurality of ultrasound transducers 48 to generate strong excitation ultrasonic waves in a short period of time to output the generated excitation ultrasonic waves to the tissue of the diagnosis target, and then a detection pulse (hereinafter, also referred to as track pulse) is further generated in the pulse generating circuit 158 and the generated detection pulses are supplied from the transmission circuit 144 to the plurality of ultrasound transducers 48 to output detection ultrasonic waves to the tissue, the temporal average intensity Ispta.$\alpha$ is further increased. Accordingly, after the detection ultrasonic waves are output, the pause period (freeze period) is provided.

In this manner, during the execution period of the ultrasound diagnosis in which the hardness of the tissue of the diagnosis target is evaluated, after strong excitation ultrasonic waves are output from the plurality of ultrasound transducers 48 to the tissue in a short period of time, or after strong excitation ultrasonic waves are output in a short period of time and then the detection ultrasonic waves are further output to the tissue, the attenuated spatial peak temporal average intensity Ispta.$\alpha$ is increased and exceeds or may exceed the limit value of 720 mW/cm$^2$ of US FDA. Accordingly, it is necessary to provide the pause period (freeze period), which results in a decrease in a frame rate of the ultrasound diagnosis.

Meanwhile, in the present invention, in the pause period, to reduce the temporal average intensity Ispta.$\alpha$, the transmission circuit 144 (pulse generating circuit 158) is controlled to generate a polarization driving pulse, which has a pulsed driving voltage, and the generated polarization driving pulses are supplied to the plurality of ultrasound transducers 48 of the ultrasound transducer array 50 to perform a polarization process on each ultrasound transducer 48.

More specifically, in the present invention, the CPU 152 is connected to the pulse generating circuit 158 of the transmission circuit 144, and during the execution period of the ultrasound diagnosis, after an excitation pulse (push pulse) is generated in the pulse generating circuit 158, and the generated excitation pulses are supplied from the transmission circuit 144 to the plurality of ultrasound transducers 48 of the ultrasound transducer array 50 to generate strong excitation ultrasonic waves in a short period of time to output the generated the excitation ultrasonic waves to the tissue of the diagnosis target, or after push pulses are supplied to the plurality of ultrasound transducers 48 and then a detection pulse (track pulse) is further generated in the pulse generating circuit 158 and the generated detection pulses are supplied from the transmission circuit 144 to the plurality of ultrasound transducers 48 to generate excitation ultrasonic waves and then detection ultrasonic waves to sequentially output the generated the excitation ultrasonic waves and the detection ultrasonic waves to the tissue of the diagnosis target, neither the transmission of the push pulse nor the transmission of the track pulse is performed, that is, in a pause period in which neither the output of the excitation ultrasonic wave nor the output of the detection ultrasonic wave is performed, the CPU 152 controls the transmission circuit 144 (pulse generating circuit 158) to generate a polarization driving pulse, which has a pulsed driving voltage, to supply the generated polarization driving pulses to the plurality of ultrasound transducers 48 of the ultrasound transducer array 50 to perform a polarization process on each of ultrasound transducers 48.

In the present invention, the polarization driving pulse is generated by the transmission circuit 144 that generates a diagnostic driving pulse such as a push pulse for exciting the tissue of the diagnosis target to displace the tissue or to generate the shear wave, a track pulse for detecting a strain due to the displacement of the tissue or the shear wave, or an image driving pulse for acquiring an ultrasound image of the diagnosis target. That is, the transmission circuit 144 has the same circuit configuration as an existing transmission circuit that does not have a new circuit configuration for generating the polarization driving pulse.

Here, the transmission circuit 144 has a settable voltage range in which at least two driving voltages of a hardness evaluation driving voltage for a push pulse and a track pulse, an image driving voltage for an image driving pulse, or a polarization driving voltage for a polarization driving pulse can be set. In a case where the hardness evaluation of the tissue is performed, voltage is set to the hardness evaluation driving voltage within the settable voltage range, in a case where the ultrasound image is acquired, voltage is set to the image driving voltage within the settable voltage range, and in a case where the polarization process is performed, voltage is set to the polarization driving voltage, which is different from the hardness evaluation driving voltage and the image driving voltage within the same settable voltage range. In the present invention, the polarization driving voltage is preferably set to voltage higher than the hardness evaluation driving voltage and the image driving voltage, more preferably to a higher voltage within the settable voltage range, and most preferably to the upper limit voltage.

In addition, the polarization driving pulse (main lobe) is a driving pulse in a frequency band different from the probe frequency band of the diagnostic driving pulse such as the push pulse, the track pulse, and the image driving pulse.

Therefore, the driving voltage applied to the ultrasound transducer 48 in a case of polarization process is different from the diagnostic driving voltage applied to the ultrasound transducer 48 in a case of ultrasound diagnosis such as a case of hardness evaluation of the tissue and a case of acquisition of an ultrasound image, and can be said to be a higher voltage than the diagnostic driving voltage applied to the ultrasound transducer 48 in a case of ultrasound diagnosis. In addition, the polarization driving pulse wave applied to the ultrasound transducer 48 in a case of polarization process is generated by the same transmission circuit 144 as for the diagnostic driving pulse wave such as the push pulse wave, the track pulse wave, and the image driving pulse wave applied to the ultrasound transducer 48 in a case of ultrasound diagnosis such as a case of hardness evaluation of the tissue and a case of acquisition of an ultrasound image, and it can be said that the polarization driving pulse wave has a polarization driving voltage different from that of the diagnostic driving pulse wave such as the push pulse wave, the track pulse wave, and the image driving pulse wave within the same settable voltage range as the diagnostic driving pulse wave, and is a driving pulse having a frequency different from the probe frequency band for ultrasound diagnosis. As described above, in the repolarization process in which the polarization process is performed, although the polarization driving voltage is higher than the diagnostic driving voltage, the polarization driving pulse is a driving pulse having a frequency different from the probe frequency band of the diagnostic driving pulse, thus it can be said that an ultrasonic wave is hardly output from the ultrasound transducer 48 on which the polarization process is performed, and the influence on the spatial peak temporal average intensity is suppressed to be low.

From the above, the present invention has an existing transmission circuit configuration. Using the transmission circuit 144 for the same driving pulse output as the ultrasound diagnosis, a polarization driving pulse, which has a driving voltage within the same settable voltage range as the diagnostic driving pulse for the ultrasound diagnosis and has a frequency different from the probe frequency band, is output, and polarization process of the ultrasound transducer 48 of the ultrasound endoscope 12 is performed in a pause period after an application of the push pulse in a case of hardness evaluation of the tissue or after the application of the push pulse and a subsequent application of the track pulse.

The magnitude (voltage value or potential) of the driving voltage of a polarization driving pulse is set to an appropriate value satisfying the conditions for obtaining the repolarization effect, within the settable voltage range of the transmission circuit 144, by the CPU 152 in accordance with the specification of the ultrasound transducer 48 (specifically, the thickness and the material of the ultrasound transducer 48) provided in the ultrasound endoscope 12 connected to the ultrasound processor device 14. In addition, a supply time of the driving voltage of the polarization driving pulse needs to be a time within a pause period in which no driving pulse is emitted after the transmission of the push pulse or after the transmission of the push pulse and a subsequent transmission of the track pulse. However, the supply time is set to an appropriate value satisfying the conditions for obtaining the repolarization effect by the CPU 152 in accordance with a value of an attenuated spatial peak temporal average acoustic output generated in the ultrasound transducer 48 after the transmission of the driving pulse that affects a state of the ultrasound transducer 48, particularly the attenuated spatial peak temporal average intensity, or further, in accordance with the cumulative driving time and the specification of the ultrasound transducer 48 (specifically, the thickness and the material of the ultrasound transducer 48). Thereafter, the CPU 152 performs the polarization process based on the values of the attenuated spatial peak temporal average acoustic output and the attenuated spatial peak temporal average intensity, or further, based on the cumulative driving time and the set value.

In the present invention, as shown in FIG. 5, a case in which the push pulse is transmitted and then the track pulse is transmitted, and then repolarization is performed will be described.

In an example shown in FIG. 5, a time from the transmission of the push pulse (n=1) to immediately before the start of the transmission of the track pulse is defined as a push pulse period Tx and is 0.2 to 5 ms. The push pulse period Tx is the same as the push pulse transmission period 1 shown in FIG. 13.

Next, in FIG. 5, a time from the start of the transmission of the track pulse (n=10000) to the end of the transmission of the track pulse and immediately before the start of the polarization process is defined as a track pulse period Ty and is 20 ms. The track pulse period Ty is the same as the track pulse transmission/reception period 2 shown in FIG. 13.

In addition, a time from the start of the polarization process (the transmission of the polarization driving pulse) to the start of a subsequent transmission of the push pulse is defined as a polarization process period Tz, and is a pause period of the driving pulse in which the push pulse and the track pulse are not transmitted. The polarization process period Tz is the same as the pause period 3 shown in FIG. 13 in the sense that it is a pause period of the driving pulse. Meanwhile, since the polarization process may not be performed in the entire period of the polarization process period Tz, in this case, the polarization process period Tz is a sum of the time during which the polarization process is performed and the pause time during which neither the transmissions of the push pulse and the track pulse nor the polarization process by the transmission of the polarization driving pulse is performed, that is, all operations are completely paused.

Here, in the push pulse period Tx, an acoustic output value, that is, a value of attenuated spatial peak temporal average acoustic output generated in the ultrasound transducer 48 in a case of the transmission of push pulses to the plurality of ultrasound transducers 48 of the ultrasound transducer unit 46 is defined as X (mJ/cm$^2$). The attenuated spatial peak temporal average acoustic output represents energy of ultrasonic waves radiated from the plurality of ultrasound transducers 48 of the ultrasound transducer unit 46 to a unit area perpendicular to a traveling direction of the ultrasonic waves in a unit time.

Next, in the track pulse period Ty, the value of attenuated spatial peak temporal average acoustic output generated in the ultrasound transducer 48 in a case of transmission of track pulse to the ultrasound transducer 48 is defined as Y (mJ/cm$^2$).

In addition, in the polarization process period Tz, the value of attenuated spatial peak temporal average acoustic output (hereinafter, also simply referred to as temporal average acoustic output) generated in the ultrasound transducer 48 in a case of polarization process to the ultrasound transducer 48 is defined as Z (mJ/cm$^2$).

As described above, in a case where the push pulse period is defined as Tx, the track pulse period is defined as Ty, and the polarization process period is defined as Tz, and the acoustic output values of the respective periods, that is, the values of the temporal average acoustic output are defined as X, Y, and Z, respectively, the attenuated spatial peak temporal average intensity Ispta.$\alpha$ (mW/cm$^2$) of the total thereof is calculated by Equation (1).

$$Ispta.\alpha = (X + Y + Z)/(Tx + Ty + Tz) \tag{1}$$

In a case where the temporal average intensity Ispta.$\alpha$ obtained in this manner is 720 mW/cm$^2$ or less, a subsequent transmission of the push pulse or another mode scan for acquiring an ultrasound image can be restarted.

In the present invention, the CPU 152 calculates the temporal average intensity Ispta.$\alpha$ based on the values X, Y, and Z of the temporal average acoustic output. In accordance with the acoustic output value, that is, values X, Y, and Z of attenuated spatial peak temporal average acoustic output generated in a case of the transmission of the driving pulse, that is, the push pulse, the track pulse, and the polarization driving pulse, specifically, in accordance with the calculated temporal average intensity Ispta.$\alpha$ by calculating the attenuated spatial peak temporal average intensity Ispta.$\alpha$ from the acoustic output values X, Y, and Z, that is, after comparing the calculated temporal average intensity Ispta.$\alpha$ and the limit value of 720 mW/cm$^2$ of US FDA, the CPU 152 sets the required polarization process time within a polarization process period Tz, which is a pause period in which the push pulse and the track pulse are not transmitted.

The values X, Y, and Z in each mode (each period Tx, Ty, and Tz) can be calculated as follows. For example, in a case where the value of attenuated spatial peak temporal average acoustic output is Y, in the track pulse period Ty, 1) An attenuated spatial peak temporal average acoustic output value y (mJ/cm$^2$) of one pulse is calculated.

2) In the period Ty, the number of times N of driving the pulse of above 1) is obtained, and the value Y is obtained by multiplying the value y by the number of times N (Y=N*y).

The values X and Z can also be obtained in the same manner.

There is a possibility that a plurality of pulses are included in the values X, Y, and Z depending on a mode, and the values may be obtained by a method in which the values (x, y, z) per pulse are fixed in the device and the values are calculated as appropriate, or a method in which a condition table of predetermined combinations of pulse is prepared and the condition table is referred to.

The push pulse period Tx and the track pulse period Ty vary depending on a position and/or a range of the tissue of the diagnosis target or the observation target part. For this reason, the push pulse period Tx, the track pulse period Ty, and the values X and Y of temporal average acoustic output are determined depending on the region of interest (ROI) set by the operator (user). Therefore, the CPU 152 can perform the control of the polarization process period Tz and the value Z of temporal average acoustic output in accordance with the push pulse period Tx, the track pulse period Ty, and the values X and Y. That is, in a case where the polarization process is performed in response to an operation of an operator on the tissue of the diagnosis target, the CPU 152 calculates the acoustic output value (X+Y+Z) of the ultrasound transducer 48 in the polarization process, specifically, before (immediately before) the polarization process, and controls the polarization process time during which the polarization process is performed within the polarization process period Tz (pause period 3) such that the acoustic output value (X+Y+Z) is equal to or less than a preset index value of acoustic output.

Further, the CPU 152 calculates a level of depolarization of the ultrasound transducer 48 generated by the transmissions of the push pulse and the track pulse from a transmission time of the push pulse and the track pulse, calculates an acoustic output value (X+Y+Z) immediately before the polarization process from the calculated level of depolarization, and controls the polarization process time within the polarization process period Tz (pause period 3) in accordance with the calculated acoustic output value (X+Y+Z).

The polarization process time in which the calculated acoustic output value (X+Y+Z) of the ultrasound transducer 48 immediately before the polarization process is equal to or less than the index value, and the polarization process time corresponding to the acoustic output value (X+Y+Z) are set in advance in the CPU 152.

Hereinafter, a specific example is shown.

For example, in a case where X: 50 mJ/cm², Y: 20 mJ/cm², and Z: 2 mJ/cm², $$X+Y+Z=72 \text{ mJ/cm}^2, \text{ and}$$

$$Tx+Ty=0.05 \text{ s,}$$

in a case where Tz is less than 0.05 s, Ispta.a exceeds an upper limit value.

Here, Z=2 may be a fixed value (a value that can be an upper limit value), or Z may be calculated from the current depolarization state. In a case where the required strength of the polarization process is determined, Z is determined, and the total time is controlled by Tz to suppress Ispta.α to be 720 mW/cm² or less.

Meanwhile, ARFI imaging, which evaluates the hardness of the tissue of the diagnosis target from the displacement (strain) of the tissue due to the application of the push pulse, may consist of the push pulse period Tx, the track pulse period Ty, and the polarization process period Tz as shown in FIG. 5.

In such ARFI imaging, under the control of the CPU 152, the push pulse (first transmission signal) is transmitted from the transmission circuit 144 to the ultrasound transducer 48, and the excitation ultrasonic wave generated in the ultrasound transducer 48 is transmitted to the tissue of the diagnosis target to excite and displace the tissue. Then, the track pulse (second transmission signal) for detecting the displacement (strain) of the tissue is transmitted to the ultrasound transducer 48, the detection ultrasonic wave generated in the ultrasound transducer 48 is transmitted to the displaced tissue, the reflected wave of the detection ultrasonic wave corresponding to the displacement (strain) of the tissue is received by the ultrasound transducer 48, and a reception signal (second reception signal) based on the reflected wave received by the ultrasound transducer 48 is output from the reception circuit 142. Then, in the evaluation unit 168, the displacement (strain) of the tissue is calculated based on the second reception signal to evaluate the hardness of the tissue based on the displacement (strain).

In this case, the pause period of the push pulse and the track pulse is the polarization process period Tz, and is a period from the end of the transmission of the track pulse (second transmission signal) to the start of the subsequent transmission of the first transmission signal. In the present invention, a trigger generating circuit that detects the end of the transmission of the track pulse (second transmission signal) and that generates a trigger signal may be provided, and the polarization process may be started based on the trigger signal.

In the ARFI imaging, under the control of the CPU 152, the excitation ultrasonic wave generated from the ultrasound transducer 48 to which the push pulse (first transmission signal) has been transmitted from the transmission circuit 144 may be transmitted to the tissue of the diagnosis target to excite and displace the tissue. Then, the reflected wave of the excitation ultrasonic wave from the tissue due to the displacement (strain) may be received by the ultrasound transducer 48, a reception signal (first reception signal) based on the reflected wave received by the ultrasound transducer 48 may be output from the reception circuit 142, and in the evaluation unit 168, the displacement (strain) of the tissue may be calculated based on the first reception signal to evaluate the hardness of the tissue based on the displacement (strain).

Consequently, in this case, the track pulse is not transmitted. Therefore, since the track pulse period Ty is 0 (Ty=0) and the value Y of attenuated spatial peak temporal average acoustic output is also 0 mJ/cm² (Y=0), in various examples described above from the example shown in FIG. 5, Ty=0 and Y=0 may be set.

Accordingly, in such ARFI imaging, in a case where the attenuated spatial peak temporal average intensity Ispta.α (mW/cm²) is calculated, in Equation (1), Ispta.α may be calculated by setting Ty=0 and Y=0.

In the ARFI imaging, the polarization process period Tz starts immediately after the push pulse period Tx. Therefore, the pause period of the push pulse is the polarization process period Tz, and is a period from the end of the transmission of the first transmission signal to the start of the subsequent transmission of the first transmission signal. In the present invention, a trigger generating circuit that detects the end of the transmission of the push pulse (first transmission signal) and that generates a trigger signal may be provided, and the polarization process may be started based on the trigger signal.

Meanwhile, in shear wave imaging, an acoustic velocity of a transverse wave (shear wave) generated in the tissue of the diagnosis target due to the application of the push pulse is detected by the track pulse to evaluate the hardness of the tissue from the detected acoustic velocity. The shear wave imaging consists of the push pulse period Tx, the track pulse period Ty, and the polarization process period Tz as shown in FIG. 5. In such shear wave imaging, under the control of the CPU 152, the push pulse (first transmission signal) is transmitted from the transmission circuit 144 to the ultrasound transducer 48, and the excitation ultrasonic wave generated in the ultrasound transducer 48 is transmitted to the tissue of the diagnosis target to excite the tissue to generate a shear wave. Then, the track pulse (third transmission signal) for detecting the acoustic velocity of the generated shear wave is transmitted to the ultrasound transducer 48, the detection ultrasonic wave generated in the ultrasound transducer 48 is transmitted to the tissue in which the shear wave is generated, the reflected wave of the detection ultrasonic wave is received by the ultrasound transducer 48 in accordance with the acoustic velocity of the shear wave, and a reception signal (third reception signal) based on the reflected wave received by the ultrasound transducer 48 is output from the reception circuit 142. Then, in the evaluation unit 168, the acoustic velocity of the shear wave generated in the tissue is calculated based on the third reception signal to evaluate the hardness of the tissue based on the calculated acoustic velocity.

In this case, the pause period of the push pulse and the track pulse is the polarization process period Tz, and is a period from the end of the transmission of the third transmission signal to the start of the subsequent transmission of the first transmission signal. In the present invention, a trigger generating circuit that detects the end of the transmission of the track pulse (third transmission signal) and that generates a trigger signal may be provided, and the polarization process may be started based on the trigger signal.

Meanwhile, in the guidance of US FDA, a spatial peak temporal average intensity Ispta represents acoustic energy that passes through a unit area perpendicular to a traveling direction of a sound wave (ultrasonic wave) in a unit time, and is defined as a value (mW/cm$^2$) of a temporal average intensity at a point in a sound field where the temporal average intensity is maximized or maximized in a specific region, and an attenuated spatial peak temporal average intensity Ispta$_{.3}$ is defined as a value of Ispta that is decreased (attenuated) by 0.3 dBcm$^{-1}$MHz$^{-1}$ in consideration of acoustic attenuation of a soft tissue.

The spatial peak temporal average intensity Ispta can be obtained as follows.

First, a pulse square integral (pulse intensity integral) PII (mJ/cm$^2$) of the driving pulse can be obtained by integrating the squares of the observed entire pulse, and can be represented by Equation (2).

$$PII = \frac{\sum \{p(t)\}^2 \cdot \Delta t}{\rho \cdot c} \tag{2}$$

Here, p(t) is an instantaneous sound pressure (MPa), $\Delta t$ is a sample interval (µs), $\rho$ is a density (kg/m$^3$), and c is an acoustic velocity (m/s) in water.

In a case where unit conversion of the pulse square integral PII is performed with $\rho$=1000 kg/m$^3$, it can be seen that the unit is (mJ/cm$^2$) from Equation (3).

$$PII = \tag{3}$$
$$\frac{MPa^2 \cdot \mu s}{10^3 kg/m^3 \cdot m/s} = \frac{10^6 Pa \cdot kg \cdot (m^2/s^2) \cdot s}{10^3 kg/m^3 \cdot m/s} = 10^3 Pa \cdot m = 10^{-1} \cdot J/cm^2$$

Next, the spatial peak temporal average intensity Ispta can be calculated by Equation (4) or (5).

First, Ispta (mW/cm$^2$) is differently calculated depending on whether the mode is a scan mode (B mode, CD mode) or a non-scan mode (M mode, PW mode).

In a Case of the Non-Scan Mode, $$Ispta = PII \times PRF \tag{4}$$

PRF: pulse repetition frequency (kHz)
In a Case of the Scan Mode $$Ispta = PII \times k \times FR \tag{5}$$

FR: frame rate (frame/s)
k: weighting of overlap of beams

As described above, the attenuated spatial peak temporal average intensity Ispta.$\alpha$ (mW/cm$^2$) can be obtained from the spatial peak temporal average intensity Ispta obtained according to Equation (4) or (5) by Equation (6)

$$I_{spta,\alpha} = I_{spta} \cdot 10^{-\alpha \cdot z \cdot f_{awf}/10} \tag{6}$$

Ispta.$\alpha$: attenuated spatial peak temporal average intensity (mW/cm$^2$)
Ispta: spatial peak temporal average intensity (mW/cm$^2$)
$\alpha$: acoustic attenuation coefficient
z: distance from external opening of probe to point of interest
$f_{awf}$: acoustic operation frequency As described above, based on the obtained attenuated spatial peak temporal average intensity Ispta.$\alpha$, on the ultrasound transducer 48 to which the push pulse is transmitted and on the ultrasound transducer 48 to which the push pulse is transmitted and then the track pulse is transmitted, a polarization process time during which the polarization process is performed can be set, and the driving voltage (polarization driving voltage) of the polarization driving pulse, the driving frequency of the polarization driving pulse, and the like in a case where the polarization process is performed can also be set.

The attenuated spatial peak temporal average intensity Ispta.$\alpha$ can also be obtained from a pulse square integral (pulse intensity integral) PII (mJ/cm$^2$) of the driving pulse as follows.

First, by performing the same calculation as in Equation (6), an attenuated pulse intensity integral PII.$\alpha$ (mJ/cm$^2$) can be obtained from the pulse intensity integral PII (mJ/cm$^2$) by Equation (7).

$$PII.\alpha = PII \cdot 10^{-\alpha \cdot z \cdot f_{awf}/10} \tag{7}$$

Next, as in Equation (8), the attenuated spatial peak temporal average intensity Ispta.$\alpha$ can be obtained by multiplying the attenuated pulse intensity integral PII.$\alpha$ by the number of times N the driving pulse is transmitted by the ultrasound transducer 48 and dividing the result by a total transmission time T during which the driving pulse is transmitted.

$$Ispta.\alpha = PII.\alpha \cdot N/T \tag{8}$$

Here, the values X, Y, and Z of the attenuated spatial peak temporal average acoustic output correspond to PII.$\alpha$·N in Equation (8).

The total transmission time T in above (8) needs to be indicated in a time of one frame, and in a case of a single mode, the time of one frame is applied to T in above (8), but in a case of a mode in which various transmissions are mixed, PII.$\alpha$·N is divided by the total time including all modes.

The attenuated spatial peak temporal average intensity Ispta.$\alpha$ can be obtained from X, Y, and Z in each mode (each period Tx, Ty, and Tz) according to Equation (9).

$$Ispta.\alpha = X/(Tx + Ty + Tz) + Y/(Tx + Ty + Tz) + Z/(Tx + Ty + Tz) = \qquad (9)$$

$$(X + Y + Z)/(Tx + Ty + Tz)$$

That is, in the present invention, the CPU (control circuit) 152 controls the transmission circuit 144 (pulse generating circuit 158) to generate the diagnostic driving pulses (transmission signal) such as the push pulses or the track pulses applied to the plurality of ultrasound transducers 48, which generate the excitation ultrasonic wave or further generate the detection ultrasonic wave, in a case where diagnosis is performed based on the evaluation of the hardness of the tissue of the diagnosis target, or to generate the diagnostic driving pulses applied to the plurality of ultrasound transducers 48, which generate the ultrasonic waves for acquiring the ultrasound image, in a case where the acquisition of the ultrasound image is performed.

On the other hand, in the case of performing polarization process, in order to perform polarization process of the plurality of ultrasound transducers 48, the CPU (control circuit) 152 controls a transmission circuit 144 to generate a polarization driving pulse, which has a frequency different from the probe frequency band as an ultrasound probe (ultrasound transducer unit 46) for acquiring an ultrasound image and has a polarization driving voltage different from that of the diagnostic driving pulse within the same settable voltage range as the diagnostic driving pulse.

As a result, in the present invention, in the case of performing polarization process after the application of the diagnostic driving pulse, the polarization driving pulse is applied to the plurality of ultrasound transducers 48, and the polarization process of the plurality of ultrasound transducers 48 is performed by the polarization driving pulse.

Next, a pulse waveform and a driving waveform (transmission waveform) of a polarization driving pulse (transmission wave for polarization) transmitted from the transmission circuit 144 to the ultrasound transducer 48 in the present invention will be described.

FIGS. 6A and 6B are graphs of an example of a driving waveform of a polarization driving pulse transmitted from the transmission circuit shown in FIG. 4, and are graphs showing the relationship between the sensitivity and the frequency of the driving waveform. The driving waveform shown in FIG. 6A is a waveform of one unipolar wave having a frequency of 1.25 MHz.

In the present invention, the driving waveform of the polarization driving pulse is not particularly limited but has a unipolar waveform shown in FIG. 6A, and it is preferable to perform polarization process of the ultrasound transducer 48 using a polarization driving pulse having a driving waveform having a frequency characteristic shown by the solid line in FIG. 6B. In the example shown in FIG. 6B, for example, at a sensitivity level of −20 dB or more, the probe frequency band for acquiring an ultrasound image is about 2.7 MHz to about 11.7 MHz as shown by the broken line, while the band of the main lobe of the driving waveform of the polarization driving pulse shown by the solid line is about 2.3 MHz or less. That is, the band characteristic of the frequency of the polarization driving pulse and the band characteristic of the frequency of the diagnostic driving pulse do not overlap each other at a sensitivity level of −20 dB or more.

That is, in the present invention, as shown in FIG. 6B, in the driving waveform of the polarization driving pulse, it is preferable that the frequency band of the main lobe and the probe frequency band shown by the broken line do not overlap each other at a sensitivity level of −20 dB or more. In addition, it is preferable that the frequency band of the main lobe is lower than the probe frequency band at a sensitivity level of −20 dB or more. The reason is that, in the polarization process, it is necessary to reduce an influence on the ultrasound image by preventing excessive ultrasound output and to reduce an influence on the body cavity of the subject due to temperature rise by preventing the temperature rise. In particular, the upper limit temperature of the distal end portion of the ultrasound endoscope 12 inserted into the body cavity of the subject is strictly limited so as not to affect the body cavity and the like, and it is necessary to prevent the temperature rise.

In the present invention, since the polarization driving pulse (main lobe) is transmitted outside the probe frequency band, the energy input to the ultrasound transducer 48 is reduced. Therefore, the temperature rise can be suppressed. In addition, since the outside of the probe frequency band is the outside of a resonance band in which the ultrasound transducer 48 resonates. Accordingly, the output sound pressure is reduced even though the polarization driving pulse (main lobe) is applied to the ultrasound transducer 48.

In the driving waveform of the polarization driving pulse shown in FIG. 6B, it can be seen that, in addition to the main lobe, within the probe frequency band, accompanied by the main lobe, one or more side lobes similarly shown by the solid line (in the example shown in FIG. 6B, four side lobes) are generated. As shown in FIG. 6B, it is preferable that all the maximum sensitivities of the side lobes within the probe frequency band are equal to or less than −10 dB and the average sensitivity of the side lobes is equal to or less than −20 dB. The reason is as follows.

In general, the specification of the frequency characteristic of the probe is expressed in the −20 dB band of the transmission and reception sensitivity. This is because it is determined that the signal of $\frac{1}{10}$ or less from the peak of the sensitivity hardly affects an image. On the other hand, the band of the transmission wave is different from that in the case of the probe. Since only a transmission portion is taken into consideration, the level of 20 dB/2=10 dB is the threshold value. For this reason, −10 dB is more preferable in a case where a transmission component is considered.

Figure 7A:
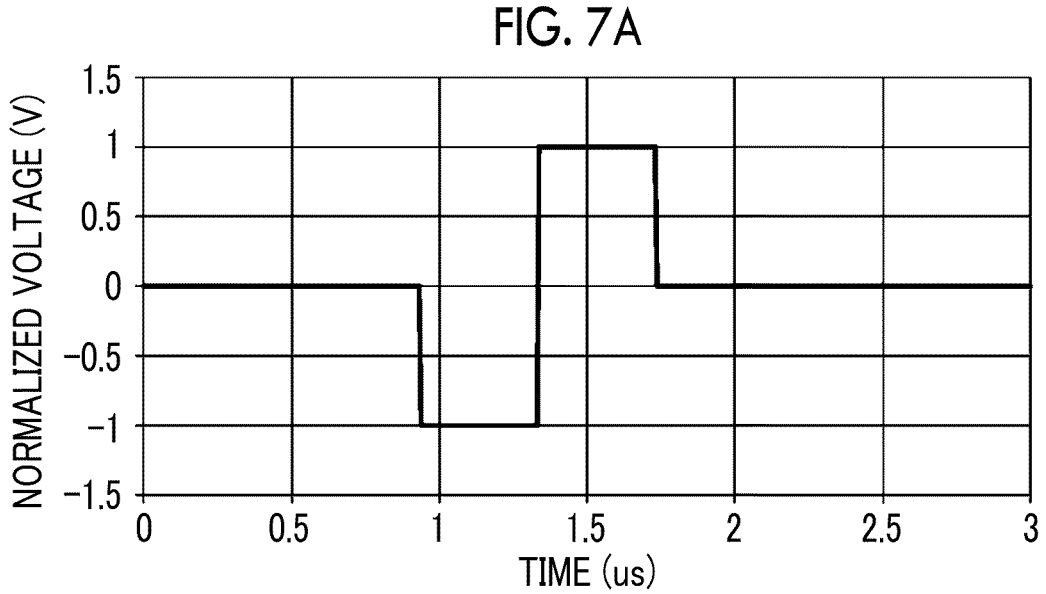
FIG. 7A is a graph showing another example of the driving waveform of the polarization driving pulse transmitted from the transmission circuit shown in FIG. 4.
Figure 7B:
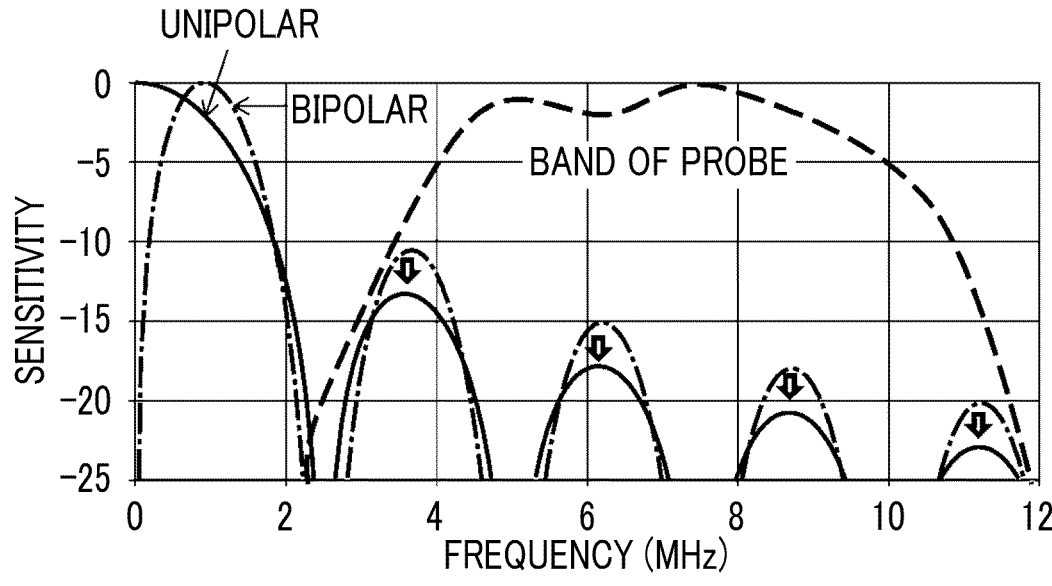
FIG. 7B is a graph showing the relationship between the frequency and the sensitivity of the driving waveform of the polarization driving pulse shown in FIG. 6A and the relationship between the frequency and the sensitivity of the driving waveform of the polarization driving pulse shown in FIG. 7A.

In the present invention, the driving waveform of the polarization driving pulse is not particularly limited, and may be a bipolar waveform shown in FIG. 7A. However, the driving waveform of the polarization driving pulse is preferably a unipolar waveform as shown in FIG. 6A. The reason is that, as in the frequency characteristic of the driving waveform shown in FIG. 7B, the sensitivity of the main lobe does not change whether the driving waveform is a unipolar waveform shown by the solid line or a bipolar waveform shown by the one-dot chain line, but the sensitivities of all of the four side lobes in the case of the unipolar waveform are lower than those in the case of the bipolar waveform.

Therefore, by forming the transmission waveform as a unipolar waveform as shown in FIG. 6A, not only the main lobe but harmonic components can be suppressed. As a result, higher effects can be expected.

Figures 8A, 8B:
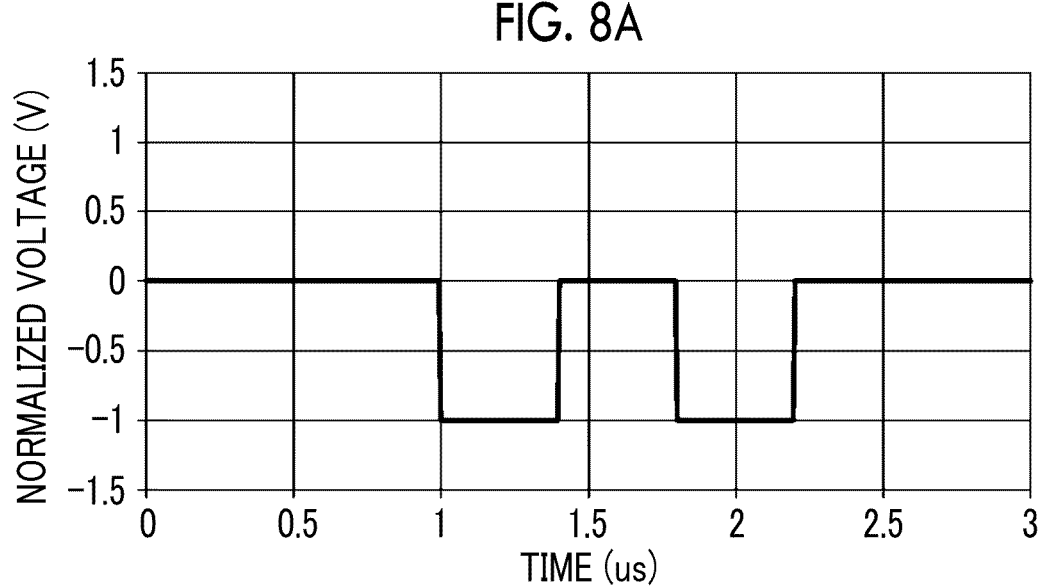
FIG. 8A is a graph showing another example of the pulse waveform of the polarization driving pulse transmitted from the transmission circuit shown in FIG. 4.
FIG. 8B is a graph showing the relationship between the frequency and the sensitivity of the driving waveform of the polarization driving pulse shown in FIG. 8A.

As shown in FIG. 8A, a plurality of unipolar waveforms may be transmitted as the polarization driving pulses. In the example shown in FIG. 8A, two pulse waves may be transmitted. The polarization driving pulse shown in FIG. 8A has a driving waveform including two pulse waves as a driving waveform of the polarization driving pulse shown in FIG. 6A. The frequency characteristic of the driving waveform of the polarization driving pulse shown in FIG. 8A is shown in FIG. 8B. The frequency characteristic of the driving waveform shown in FIG. 8B is different from the frequency characteristic of the driving waveform shown in FIG. 6B in terms of the waveform of the main lobe, but the waveform of the side lobe does not change much.

Figure 8C:
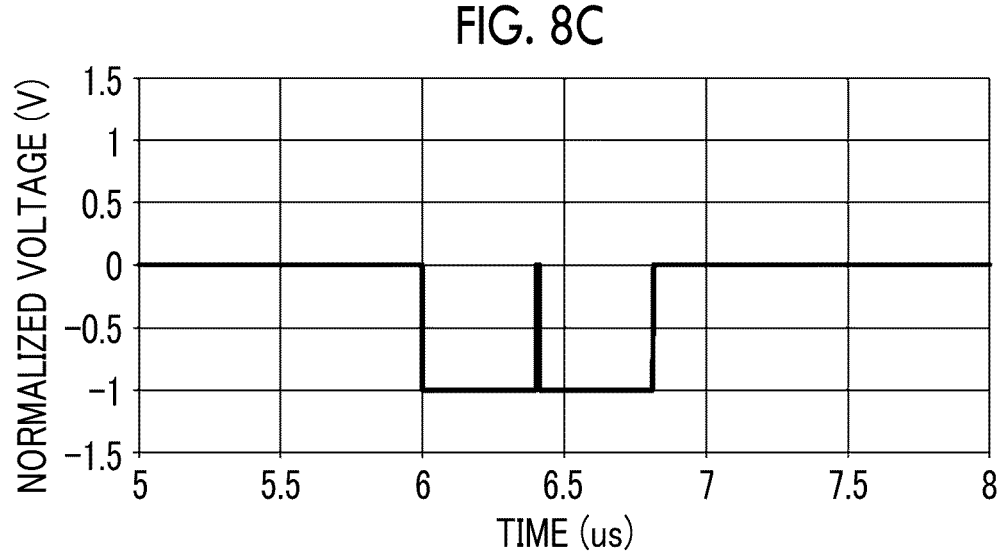
FIG. 8C is a graph showing another example of the pulse waveform of the polarization driving pulse transmitted from the transmission circuit shown in FIG. 4.

In addition, as shown in FIG. 8C, it is preferable to transmit a polarization driving pulse in which a plurality of pulse waveforms are connected to each other with the time of the minimum number of clocks between driving waveforms of the polarization driving pulse as unipolar waveforms. That is, in the present invention, it is preferable that the transmission circuit 144 outputs a plurality of unipolar waveforms as polarization driving pulses with the time of the minimum number of clocks defined in the ultrasound processor device 14 as an interval between the unipolar waveforms.

The reason is that it is optimal to apply a DC voltage for polarization process, but the DC voltage cannot be transmitted in a case where the transmission circuit 144 having an existing transmission circuit configuration is used as in the present invention.

The minimum and maximum time widths are determined depending on the type of pulser (pulse generating circuit 158) of the transmission circuit 144 of the ultrasound processor device 14 used in the ultrasound diagnostic system 10. Therefore, by using the time of the minimum number of clocks defined in the transmission circuit 144 as the minimum time width, a high repolarization effect can be expected by putting the minimum time width between a plurality of unipolar waveforms so that a polarization process waveform close to a DC voltage is obtained. The minimum time width between two unipolar pulse waveforms, that is, the strongest pulse width is determined by the specification of the pulser (pulse generating circuit 158) of the transmission circuit 144. Control to comply with this specification is provided from the above-described FPGA in the transmission circuit 144.

Figure 8D:
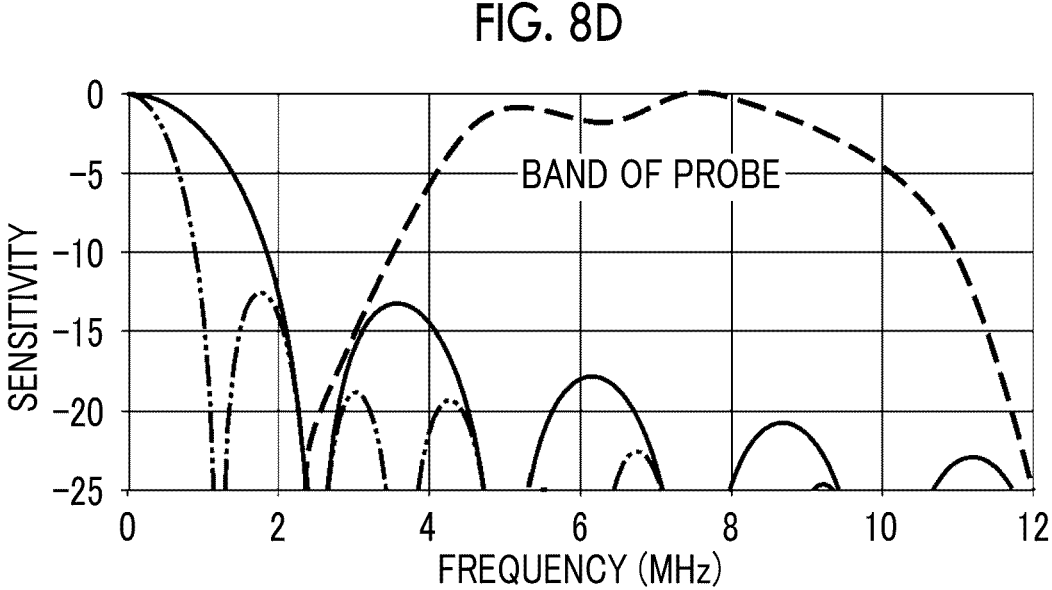
FIG. 8D is a graph showing the relationship between the frequency and the sensitivity of the driving waveform of the polarization driving pulse shown in FIG. 8C.

As shown by a two-dot chain line in FIG. 8D, by using a combination of a plurality of unipolar waveforms shown in FIG. 8C as the driving waveform of the polarization driving pulse, it is possible to reduce the maximum sensitivity of the side lobe more than in the case of the driving waveform of the polarization driving pulse including one unipolar waveform shown by the solid line in FIG. 8D.

Although not shown, regarding driving waveforms and pulse waveforms of the push pulse and the track pulse, the same frequency band as that for image visualization is essentially used. However, only the push pulse is a long burst wave that is continuously emitted for several ms, and the band is considerably narrow.

<<Operation Example of Ultrasound Diagnostic System>>

Figure 9:
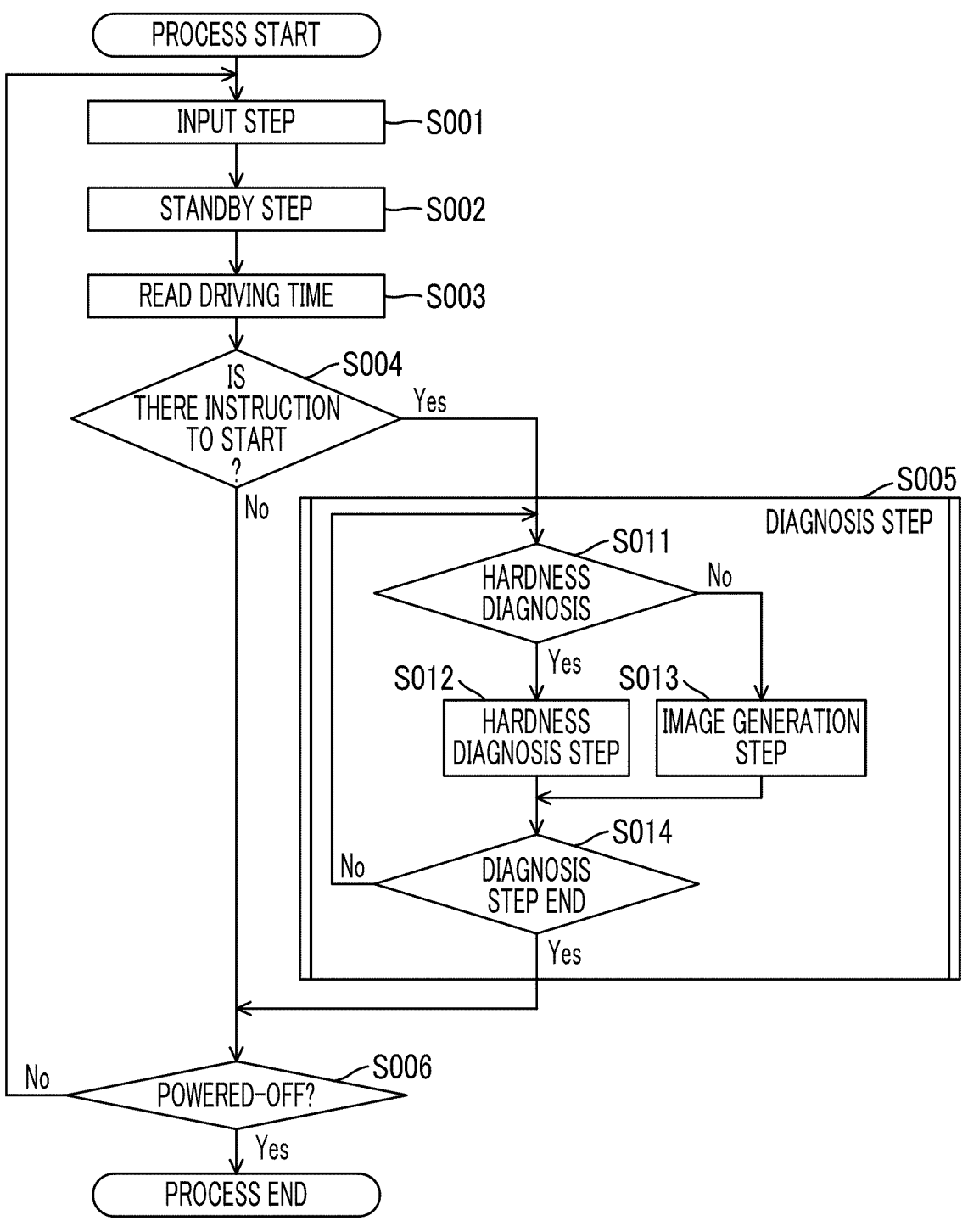
FIG. 9 is a flowchart showing the flow of the diagnosis process using the ultrasound diagnostic system shown in FIG. 1.
Figure 10:
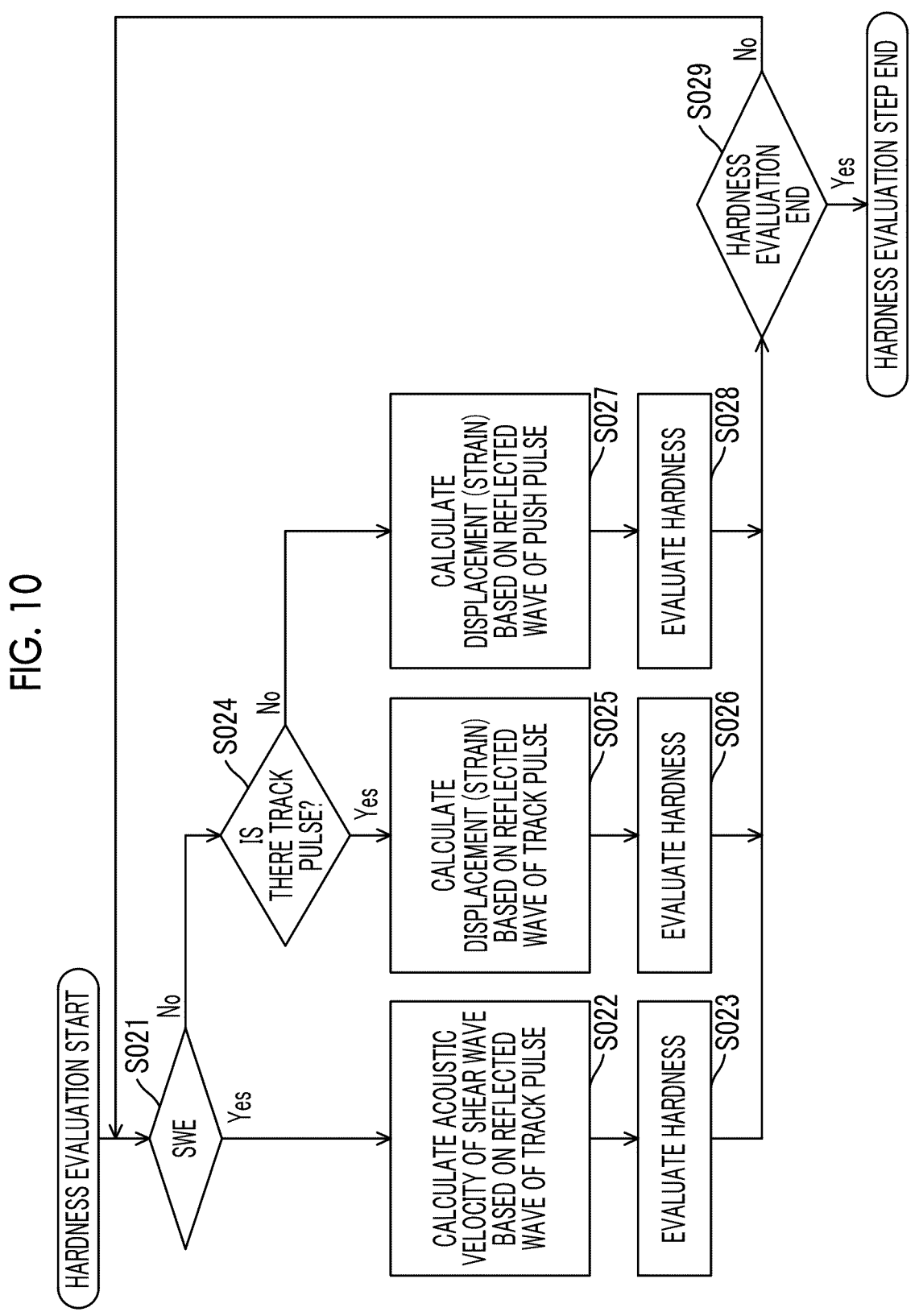
FIG. 10 is a flowchart showing a procedure of a hardness evaluation step of a tissue of a diagnosis step shown in FIG. 9.

Next, as an operation example of the ultrasound diagnostic system 10, a flow of a series of processing (hereinafter, also referred to as diagnosis process) regarding ultrasound diagnosis will be described with reference to FIGS. 9 to 11. FIG. 9 is a flowchart showing a flow of diagnosis process using the ultrasound diagnostic system 10. FIG. 10 is a flowchart showing a procedure of a hardness evaluation step of a tissue of a diagnosis step shown in FIG. 9. FIG. 11 is a flowchart showing a procedure of an image generation step of a diagnosis step shown in FIG. 9.

In a case where each unit of the ultrasound diagnostic system 10 is powered on in a state in which the ultrasound endoscope 12 is connected to the ultrasound processor device 14, the endoscope processor device 16, and the light source device 18, the diagnosis process starts with the power-ON as a trigger. In the diagnosis process, as shown in FIG. 9, an input step is performed first (S001). In the input step, the operator inputs examination information, control parameters, and the like through the console 100. In a case where the input step is completed, a standby step is performed until there is an instruction to start diagnosis (S002). Using the standby step, the CPU 152 of the ultrasound processor device 14 reads a cumulative driving time from the endoscope side memory 58 of the ultrasound endoscope 12 (S003).

Then, in a case where there is an instruction to start diagnosis from the operator (Yes in S004), the CPU 152 controls each unit of the ultrasound processor device 14 to perform a diagnosis step (S005).

In the diagnosis step, first, a determination is made as to whether or not to perform a hardness diagnosis as a diagnosis (S011), and in a case where the hardness diagnosis is performed (Yes in S011), the CPU 152 controls each unit of the ultrasound processor device 14 to perform a hardness diagnosis step (S012). In a case where the hardness diagnosis is not performed as the diagnosis (No in S011), the CPU 152 controls each unit of the ultrasound processor device 14 to perform an image generation step (S013).

In a case where the hardness diagnosis step and the image generation step end, the CPU 152 determines whether or not the ultrasound diagnosis ends (S014). In a case where the ultrasound diagnosis does not end (No in S014), the process returns to the determination step S011 as to whether or not to perform the hardness diagnosis at the start of the diagnosis step, and the hardness diagnosis step and the image generation step are repeatedly performed until the diagnosis end conditions are satisfied. As the diagnosis end conditions, for example, the operator may give an instruction to end the diagnosis through the console 100.

The hardness diagnosis step (S012) of the diagnosis step (S005) proceeds along the flow shown in FIG. 10, and a determination is made as to whether or not to perform shear wave elastography (SWE) as the hardness evaluation (S021). In a case where SWE is performed (Yes in S021), the CPU 152 controls each unit of the ultrasound processor device 14 to calculate the acoustic velocity of the shear wave generated in the tissue of the diagnosis target using the push pulse and the track pulse (S022) to evaluate the hardness of the tissue based on the calculated acoustic velocity of the shear wave (S023).

In a case where SWE is not performed as the hardness evaluation (No in S021), a determination is made as to whether the track pulse is used or not (S024). In a case where the track pulse is used (Yes in S024), the CPU 152 controls each unit of the ultrasound processor device 14 to calculate the displacement (strain) of the tissue of the diagnosis target using the push pulse and the track pulse (S025) to evaluate the hardness of the tissue based on the calculated displacement (strain) (S026).

In a case where the track pulse is not used (No in S024), the CPU 152 controls each unit of the ultrasound processor device 14 to calculate the displacement (strain) of the tissue of the diagnosis target using only the push pulse (S027) to evaluate the hardness of the tissue based on the calculated displacement (strain) (S028).

Subsequently, the CPU 152 determines whether or not the hardness evaluation ends (S029). In a case where the hardness evaluation does not end (No in S029), the process returns to the determination step S021 of whether or not to perform SWE at the start of the hardness diagnosis step (S012), and each hardness evaluation (S023, S026, S028) is repeatedly performed until the hardness evaluation end conditions are satisfied. As the hardness evaluation end conditions, for example, the operator gives an instruction to end the diagnosis through the console 100.

In the hardness diagnosis step (S012), the polarization process is simultaneously performed between a calculation step of the acoustic velocity of the shear wave (S022), a calculation step of each displacement (strain) (S025, S027), and each hardness evaluation step (S023, S026, S028).

The image generation step (S013) of the diagnosis step (S005) proceeds along the flow shown in FIG. 11. In a case where the designated image generation mode is the B mode (Yes in S031), each unit of the ultrasound processor device 14 is controlled so as to generate a B mode image (S032). In a case where the designated image generation mode is not the B mode (No in S031) but the CF mode (Yes in S033), each unit of the ultrasound processor device 14 is controlled so as to generate a CF mode image (S034). Further, in a case where the designated image generation mode is not the CF mode (No in S033) but the PW mode (Yes in S035), each unit of the ultrasound processor device 14 is controlled so as to generate a PW mode image (S036). In a case where the designated image generation mode is not the PW mode (No in S036), the process proceeds to step S037.

Subsequently, the CPU 152 determines whether or not the image generation ends (S037). In a case where the image generation does not end (No in S037), the process returns to the determination step S031 of the image generation mode, and the generation of an ultrasound image in each image generation mode is repeatedly performed until the image generation end conditions are satisfied. As the image generation end conditions, for example, the operator gives an instruction to end the diagnosis through the console 100.

On the other hand, in a case where the image generation end conditions are satisfied and accordingly the ultrasound image generation ends (Yes in S037), the CPU 152 adds the time required for the ultrasound image generation performed so far to the cumulative driving time read out from the endoscope side memory 58 in step S003, and updates the cumulative driving time stored in the endoscope side memory 58 to the cumulative driving time after the addition (S038). The image generation step (S013) ends at a point in time at which the series of steps (S031 to S038) in the image generation step end.

Subsequently, returning to FIG. 9, in a case where the diagnosis step (S005) ends, the respective units of the ultrasound diagnostic system 10 are powered-off (Yes in S006), and the diagnosis process ends. On the other hand, in a case where the respective units of the ultrasound diagnostic system 10 are maintained in a powered-on state (No in S006), the process returns to the input step S001, and the respective steps of the diagnosis process described above are repeated.

Next, in a case where the ultrasound image for performing the ultrasound diagnosis is generated, depolarization of the ultrasound transducer 48 progresses as dipoles applied to both sides of the ultrasound transducer 48 decrease according to the time for which transmission of ultrasonic waves for ultrasound image generation and reception of reflected waves are performed, that is, according to the cumulative driving time of the plurality of ultrasound transducers 48. Therefore, it is not possible to directly determine whether or not the ultrasound transducer 48 is depolarized. Accordingly, for example, it is necessary to perform the polarization process in a case where it is determined whether or not the ultrasound transducer 48 is depolarized based on the above-described cumulative driving time of the ultrasound transducers 48 and the cumulative driving time of the plurality of ultrasound transducers 48 for performing ultrasound diagnosis is equal to or longer a specified time.

As the specified time, a default value of the time may be set, or any time may be set according to the user's instruction. The specified time is any time, and may be on the order of several hours or on the order of several frame times.

It is possible to start the polarization process in a case where a button for giving an instruction to start polarization process is pressed according to the user's instruction. That is, the polarization process can be started at any timing according to the user's instruction.

The button may be an electronic button displayed within the touch panel of the console 100, or may be a mechanical button provided on the operating part 24 of the ultrasound endoscope 12.

In the contrast mode, the ultrasonic wave transmitted from the ultrasound transducer 48 is generally set to have a low output that does not destroy bubbles contained in the contrast medium. Therefore, since the S/N ratio of the image is reduced, an adverse effect of sensitivity lowering due to depolarization is likely to appear.

In a case where the depolarization of the ultrasound transducer 48 progresses and its reception sensitivity lowers, an ultrasound image acquired at a position where the display depth is relatively large is likely to have a lower S/N ratio than an ultrasound image acquired at a position where the display depth is relatively small, and the image quality is easily degraded. For this reason, it is also possible to start the polarization process in a case where the display depth of the ultrasound image for performing ultrasound diagnosis is set to a predetermined depth or more.

The display depth of the ultrasound image for performing ultrasound diagnosis can be set to, for example, a position of 4 cm in depth and a position of 10 cm in depth according to the user's instruction. For example, assuming that the predetermined depth described above is set to 5 cm, the polarization process is not started in a case where the display depth of the ultrasound image is set to a position of 4 cm in depth, and the polarization process is started in a case where the display depth of the ultrasound image is set to a position of 10 cm in depth.

Similarly, in a case where the depolarization of the ultrasound transducer 48 progresses and its reception sensitivity lowers, a B mode ultrasound image acquired at a position where the display depth is relatively large is likely to have a lower brightness than a B mode ultrasound image acquired at a position where the display depth is relatively small. For this reason, the polarization process may be started in a case where the brightness of the B mode ultrasound image, which is acquired in a state in which the display depth is set to a predetermined depth or more, is equal to or less than a predetermined brightness.

As the predetermined brightness, a default value of the brightness may be set, or any brightness may be set according to the user's instruction.

In addition, by analyzing the ultrasound image during the execution period of the ultrasound diagnosis, it is possible to recognize that the user is performing treatment while viewing the ultrasound image. For example, it is possible to recognize whether or not the user is in the process of puncture, whether or not the stent is being released, or whether or not 30 minutes have passed from the start of acquisition of the ultrasound image. In this case, during the treatment, an endoscope image and an X-ray fluoroscopic image are often used in combination. Accordingly, compared with a case where an ultrasound image is used as a main image, polarization process can be appropriately performed regardless of the image quality since attention is not paid to details of the ultrasound image. For this reason, the polarization process may be started in a case where it is recognized based on the ultrasound image that the user is performing treatment while viewing the ultrasound image.

The ultrasound diagnostic system 10 can acquire an ultrasound image and an endoscope image and display the ultrasound image and the endoscope image on the monitor 20 in various display modes.

Figures 12, 13:
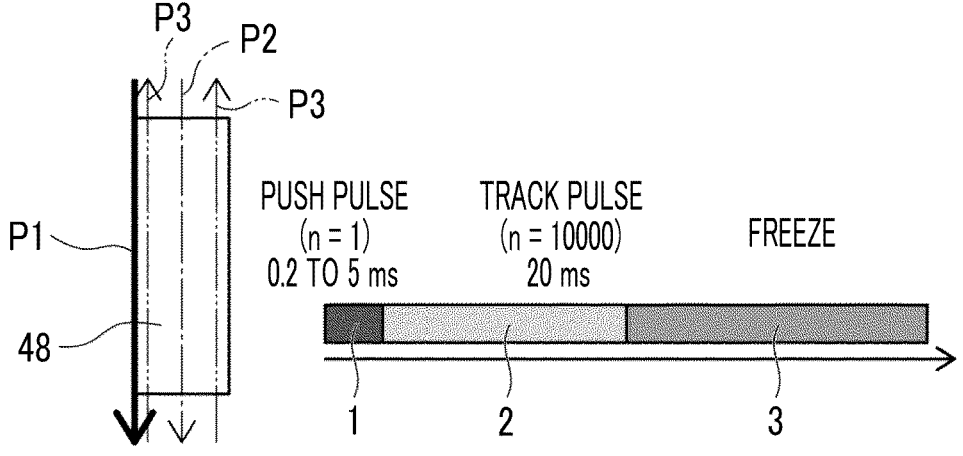
FIG. 12 is a conceptual diagram of an example showing display modes.
FIG. 13 is a diagram showing an example in which a shear wave is performed in the ultrasound system in the related art.

As shown in FIG. 12, the display modes include a first display mode in which only an ultrasound image is displayed, a second display mode in which an ultrasound image is displayed so as to be larger than an endoscope image by using picture in picture (PinP), a third display mode in which an ultrasound image is displayed so as to be smaller than an endoscope image by using the PinP similarly, and a fourth display mode in which only an endoscope image is displayed.

The first to fourth display modes can be freely switched and displayed according to the user's instruction.

Here, in the third display mode, since the ultrasound image is displayed so as to be smaller than the endoscope image, it is possible to appropriately perform the polarization process regardless of the image quality. For this reason, the polarization process may be performed in a case where the ultrasound image is displayed so as to be smaller than the endoscope image by the picture in picture while being set in the third display mode.

Although the polarization process factors have been exemplified, the polarization process may be started based on any factor other than the above-described factors.

As the end conditions of the polarization process, for example, a case where the cumulative process time of the polarization process reaches a predetermined time, a case where the user gives an instruction to end the polarization process, a case where the contrast mode is changed to another ultrasound image generation mode, a case where the display depth of the ultrasonic wave for performing ultrasound diagnosis is set to be smaller than a predetermined depth, a case where it is not recognized whether or not the user is performing treatment based on the endoscope image, a case where the brightness of the B mode ultrasound image acquired at a position where the display depth of the ultrasonic wave is relatively large becomes larger than a predetermined brightness, and a case where the third display mode is changed to another display mode can be considered. However, the polarization process may be ended according to end conditions other than those described above.

<<Effectiveness of Ultrasound Diagnostic System 10 According to Embodiment of Invention>>

During the execution period of ultrasound diagnosis, the ultrasound diagnostic system 10 immediately performs the polarization process in the pause period of the diagnostic driving pulse after the transmission of the excitation ultrasonic wave by the transmission of the push pulse, or after the transmission of the excitation ultrasonic wave by the transmission of the push pulse and then the transmission of the detection ultrasonic wave by the transmission of the track pulse. Therefore, even during the execution period of ultrasound diagnosis, it is possible to immediately reduce the attenuated spatial peak temporal average intensity Ispta.α, which is increased or increased and exceeds the limit value due to the transmission of the push pulse, or further transmission of the track pulse, or the like, to be equal to or less than the limit value. Therefore, the transmission and reception sensitivities of the plurality of ultrasound transducers 48 can always be kept satisfactory without decreasing the frame rate, without deteriorating the performance of the hardness diagnosis of the tissue of the diagnosis target, and without degrading the image quality of ultrasound image of the tissue. Therefore, it is possible to always perform the hardness diagnosis with high accuracy, and it is possible to acquire a high-quality ultrasound image.

In addition, since the ultrasound diagnostic system 10 performs the polarization process using the existing transmission circuit 144, more specifically, the pulse generating circuit 158, it is possible to perform the polarization process during the execution period of the ultrasound diagnosis without significantly changing the existing circuit.

The total number of ultrasound transducers 48 and the number of opening channels may be changed to any number. For example, in a case where the number of opening channels is the same as the total number of ultrasound transducers 48, one polarization process transmission signal for driving the 128 ultrasound transducers 48 can also be supplied instead of the two polarization process transmission signals described above. Alternatively, in a case where the number of opening channels is ¼ of the total number of ultrasound transducers 48, four polarization process transmission signals for driving the 32 ultrasound transducers 48 can also be supplied.

While the present invention has been described in detail, the present invention is not limited to the above-described embodiments, and various improvements and modifications may be made without departing from the gist of the present invention.

EXPLANATION OF REFERENCES

10: ultrasound diagnostic system
12: ultrasound endoscope
14: ultrasound processor device
16: endoscope processor device
18: light source device
20: monitor
21a: water supply tank
21b: suction pump
22: insertion part
24: operating part
26: universal cord
28a: air/water supply button
28b: suction button
29: angle knob
30: treatment tool insertion port
32a: ultrasound connector
32b: endoscope connector
32c: light source connector
34a: air/water supply tube
34b: suction tube
36: ultrasound observation portion
38: endoscope observation portion
40: distal end portion
42: bendable portion
43: soft portion
44: treatment tool outlet port
45: treatment tool channel
46: ultrasound transducer unit
48: ultrasound transducer
50: ultrasound transducer array
54: backing material layer
56: coaxial cable
58: endoscope side memory
60: FPC
74: acoustic matching layer 76: acoustic lens
82: observation window
84: objective lens
86: solid-state imaging element
88: illumination window
90: cleaning nozzle
92: wiring cable
100: console
140: multiplexer
142: reception circuit
144: transmission circuit
146: A/D converter
148: ASIC
150: cine memory
151: memory controller
152: CPU
154: DSC
158: pulse generating circuit
160: phase matching unit
162: B mode image generation unit
164: PW mode image generation unit
166: CF mode image generation unit
168: evaluation unit

What is claimed is:

1. An ultrasound diagnostic system that is configured to acquire an ultrasound image and evaluate a hardness of a tissue of a diagnosis target using an acoustic radiation pressure, the ultrasound diagnostic system comprising:

an ultrasound observation portion that is configured to transmit an ultrasonic wave including at least an excitation ultrasonic wave for exciting the tissue by the acoustic radiation pressure using an ultrasound transducer array in which a plurality of ultrasound transducers are arranged, and receive a reflected wave from the tissue; and an ultrasound processor device including a transmission circuit, which is configured to transmit an ultrasound generating transmission signal consisting of driving pulses to be applied to the plurality of ultrasound transducers to generate the ultrasonic waves from the plurality of ultrasound transducers, a reception circuit that is configured to output a reception signal of the reflected wave received by the plurality of ultrasound transducers, and a processor that is configured to evaluate the hardness of the tissue based on the reception signal, wherein the ultrasound processor device further includes a control circuit that is configured to perform the transmission of the ultrasonic wave and the reception of the reflected wave and that perform a polarization process using the transmission circuit on the plurality of ultrasound transducers that have transmitted the ultrasonic waves, in a pause period of all transmissions of ultrasonic waves after the transmission of the ultrasonic wave, and wherein the transmission circuit comprises a pulse generating circuit configured to generate the ultrasound generating transmission signal and a polarization process transmission signal, the control circuit is configured to control the pulse generating circuit within the transmission circuit to generate the ultrasound generating transmission signal consisting of the driving pulses, control the pulse generating circuit within the transmission circuit to generate the polarization process transmission signal to be transmitted to the plurality of ultrasound transducers, and after the transmission of the ultrasound generating transmission signal, which is configured to generate the ultrasonic wave including at least the excitation ultrasonic wave that generates the acoustic radiation pressure, set a polarization process time for performing the polarization process within the pause period according to an acoustic output value generated in a case of the transmissions of the ultrasound generating transmission signal and the polarization process transmission signal, and the polarization process transmission signal is transmitted from the transmission circuit to the plurality of ultrasound transducers that have transmitted at least the excitation ultrasonic wave, to perform the polarization process in the polarization process time.

2. The ultrasound diagnostic system according to claim 1, wherein the control circuit is configured to calculate the acoustic output value in the polarization process in response to an operation of a user on the tissue and control the polarization process time within the pause period such that the acoustic output value is equal to or less than a preset index value of acoustic output.

3. The ultrasound diagnostic system according to claim 2, wherein the control circuit calculates a level of depolarization of the plurality of ultrasound transducers generated by the transmission of the ultrasonic wave from a transmission time of the ultrasound generating transmission signal consisting of the driving pulse, calculates the acoustic output value in the polarization process from the calculated level of depolarization, and controls the polarization process time within the pause period according to the calculated acoustic output value.

4. The ultrasound diagnostic system according to claim 2, wherein the transmission circuit transmits a first transmission signal consisting of an excitation pulse as the ultrasound generating transmission signal to at least some of the plurality of ultrasound transducers, and generates the excitation ultrasonic waves from the plurality of ultrasound transducers and transmits the generated excitation ultrasonic waves to the tissue to press and displace the tissue, the reception circuit receives a first reception signal of the reflected wave from the tissue as the reception signal, the processor calculates the displacement of the tissue based on the ultrasound image obtained from the first reception signal to evaluate the hardness of the tissue, and the pause period is a period from an end of the transmission of the first transmission signal to a start of a subsequent transmission of the first transmission signal.

5. The ultrasound diagnostic system according to claim 2, wherein the transmission circuit transmits a first transmission signal consisting of an excitation pulse as the ultrasound generating transmission signal to at least some of the plurality of ultrasound transducers, and generates the excitation ultrasonic waves from the plurality of ultrasound transducers and transmits the generated excitation ultrasonic waves to the tissue to press and displace the tissue, and then transmits a second transmission signal consisting of a detection pulse for detecting the displacement of the tissue to at least some of the plurality of ultrasound transducers to generate a detection ultrasonic wave, and transmits the generated detection ultrasonic wave to the tissue, the reception circuit receives a second reception signal of the reflected wave of the detection ultrasonic wave from the tissue as the reception signal, the processor calculates the displacement of the tissue based on the ultrasound image obtained from the second reception signal to evaluate the hardness of the tissue, and the pause period is a period from an end of the transmission of the second transmission signal to a start of a subsequent transmission of the first transmission signal.

6. The ultrasound diagnostic system according to claim 2, wherein the transmission circuit transmits a first transmission signal consisting of an excitation pulse as the ultrasound generating transmission signal to at least some of the plurality of ultrasound transducers, and generates the excitation ultrasonic waves from the plurality of ultrasound transducers and transmits the generated excitation ultrasonic waves to the tissue to excite the tissue to generate a shear wave, and then transmits a third transmission signal consisting of a detection pulse for detecting an acoustic velocity of the shear wave to at least some of the plurality of ultrasound transducers to generate a detection ultrasonic wave, and transmits the generated detection ultrasonic wave to the tissue in which the shear wave is generated, the reception circuit receives a third reception signal of the reflected wave of the detection ultrasonic wave from the tissue as the reception signal, the processor calculates the acoustic velocity of the shear wave based on the third reception signal to evaluate the hardness of the tissue, and the pause period is a period from an end of the transmission of the third transmission signal to a start of a subsequent transmission of the first transmission signal.

7. The ultrasound diagnostic system according to claim 2, further comprising:

an ultrasound endoscope including an endoscope observation portion for acquiring an endoscope image, and the ultrasound observation portion.

8. The ultrasound diagnostic system according to claim 1, wherein the control circuit is configured to calculate a level of depolarization of the plurality of ultrasound transducers generated by the transmission of the ultrasonic wave from a transmission time of the ultrasound generating transmission signal consisting of the driving pulse, calculate the acoustic output value in the polarization process from the calculated level of depolarization, and control the polarization process time within the pause period according to the calculated acoustic output value.

9. The ultrasound diagnostic system according to claim 1, wherein the transmission circuit is configured to transmit a first transmission signal consisting of an excitation pulse as the ultrasound generating transmission signal to at least some of the plurality of ultrasound transducers, and generate the excitation ultrasonic waves from the plurality of ultrasound transducers and transmit the generated excitation ultrasonic waves to the tissue to press and displace the tissue, the reception circuit is configured to receive a first reception signal of the reflected wave from the tissue as the reception signal, the processor is configured to calculate the displacement of the tissue based on the ultrasound image obtained from the first reception signal to evaluate the hardness of the tissue, and the pause period is a period from an end of the transmission of the first transmission signal to a start of a subsequent transmission of the first transmission signal.

10. The ultrasound diagnostic system according to claim 1, wherein the transmission circuit is configured to transmit a first transmission signal consisting of an excitation pulse as the ultrasound generating transmission signal to at least some of the plurality of ultrasound transducers, and generate the excitation ultrasonic waves from the plurality of ultrasound transducers and transmits the generated excitation ultrasonic waves to the tissue to press and displace the tissue, and then transmit a second transmission signal consisting of a detection pulse for detecting the displacement of the tissue to at least some of the plurality of ultrasound transducers to generate a detection ultrasonic wave, and transmit the generated detection ultrasonic wave to the tissue, the reception circuit is configured to receive a second reception signal of the reflected wave of the detection ultrasonic wave from the tissue as the reception signal, the processor is configured to receive the displacement of the tissue based on the ultrasound image obtained from the second reception signal to evaluate the hardness of the tissue, and the pause period is a period from an end of the transmission of the second transmission signal to a start of a subsequent transmission of the first transmission signal.

11. The ultrasound diagnostic system according to claim 1, wherein the transmission circuit is configured to transmit a first transmission signal consisting of an excitation pulse as the ultrasound generating transmission signal to at least some of the plurality of ultrasound transducers, and generate the excitation ultrasonic waves from the plurality of ultrasound transducers and transmit the generated excitation ultrasonic waves to the tissue to excite the tissue to generate a shear wave, and then transmit a third transmission signal consisting of a detection pulse for detecting an acoustic velocity of the shear wave to at least some of the plurality of ultrasound transducers to generate a detection ultrasonic wave, and transmit the generated detection ultrasonic wave to the tissue in which the shear wave is generated, the reception circuit is configured to a third reception signal of the reflected wave of the detection ultrasonic wave from the tissue as the reception signal, the processor is configured to the acoustic velocity of the shear wave based on the third reception signal to evaluate the hardness of the tissue, and the pause period is a period from an end of the transmission of the third transmission signal to a start of a subsequent transmission of the first transmission signal.

12. The ultrasound diagnostic system according to claim 1, further comprising:

an ultrasound endoscope including an endoscope observation portion for acquiring an endoscope image, and the ultrasound observation portion.

13. An operation method of an ultrasound diagnostic system that is configured to acquire an ultrasound image and evaluate a hardness of a tissue of a diagnosis target using an acoustic radiation pressure, the ultrasound diagnostic system including an ultrasound observation portion, which has an ultrasound transducer array in which a plurality of ultrasound transducers are arranged, and an ultrasound processor device including a transmission circuit, which comprises a pulse generating circuit configured to generate an ultrasound generating transmission signal and a polarization process transmission signal and transmit the ultrasound generating transmission signal to the plurality of ultrasound transducers, a reception circuit, which outputs a reception signal of reflected waves received by the plurality of ultrasound transducers, and a processor, which evaluates the hardness of the tissue based on the reception signal, the operation method comprising:

a first signal generation step of controlling the pulse generating circuit within the transmission circuit to generate the ultrasound generating transmission signal consisting of driving pulses to be applied to the plurality of ultrasound transducers, to generate an ultrasonic wave from the plurality of ultrasound transducers;

a first transmission step of transmitting the ultrasound generating transmission signal generated by the pulse generating circuit within the transmission circuit to the plurality of ultrasound transducers, applying the driving pulse to the plurality of ultrasound transducers to generate the ultrasonic wave including at least an excitation ultrasonic wave that generates the acoustic radiation pressure, and transmitting the generated ultrasonic wave to the tissue;

an output step of receiving reflected waves from the tissue to which the ultrasonic wave has been delivered, via the plurality of ultrasound transducers, and outputting a reception signal based on the reflected waves received by the plurality of ultrasound transducers, from the reception circuit;

an evaluation step of evaluating the hardness of the tissue via the processor based on the reception signal output from the reception circuit;

a second signal generation step of controlling the pulse generating circuit within the transmission circuit to generate the polarization process transmission signal to be transmitted to the plurality of ultrasound transducers, to perform a polarization process on the plurality of ultrasound transducers that have transmitted the ultrasonic waves in a pause period of all transmissions of ultrasonic waves after the transmission of the ultrasonic wave;

a setting step of, in the pause period after the transmission of the ultrasound generating transmission signal, which generates the ultrasonic wave including at least the excitation ultrasonic wave that generates the acoustic radiation pressure, setting a polarization process time for performing the polarization process within the pause period according to an acoustic output value generated in a case of the transmissions of the ultrasound generating transmission signal and the polarization process transmission signal; and a polarization step of transmitting the polarization process transmission signal from the transmission circuit to the plurality of ultrasound transducers that have transmitted at least the excitation ultrasonic wave, to perform the polarization process in the polarization process time.

14. The operation method of the ultrasound diagnostic system according to claim 13, wherein the setting step is a step of calculating the acoustic output value in the polarization process in response to an operation of a user on the tissue, and setting the polarization process time within the pause period such that the acoustic output value is equal to or less than a preset index value of acoustic output.

15. The operation method of an ultrasound diagnostic system according to claim 14, wherein the setting step is a step of calculating a level of depolarization of the plurality of ultrasound transducers generated by the transmission of the ultrasonic wave from a transmission time of the ultrasound generating transmission signal consisting of the driving pulse, calculating the acoustic output value in the polarization process from the calculated level of depolarization, and controlling the polarization process time within the pause period according to the calculated acoustic output value.

16. The operation method of an ultrasound diagnostic system according to claim 14, wherein the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to press and displace the tissue, the output step is a step of receiving a first reception signal based on the reflected wave from the tissue as the reception signal by the reception circuit, and outputting the first reception signal based on the reflected wave from the reception circuit, the evaluation step is a step of calculating the displacement of the tissue based on the ultrasound image obtained from the first reception signal to evaluate the hardness of the tissue via the processor, and the pause period is a period from an end of the transmission of the first transmission signal to a start of a subsequent transmission of the first transmission signal.

17. The operation method of the ultrasound diagnostic system according to claim 13, wherein the setting step is a step of calculating a level of depolarization of the plurality of ultrasound transducers generated by the transmission of the ultrasonic wave from a transmission time of the ultrasound generating transmission signal consisting of the driving pulse, calculating the acoustic output value in the polarization process from the calculated level of depolarization, and controlling the polarization process time within the pause period according to the calculated acoustic output value.

18. The operation method of the ultrasound diagnostic system according to claim 13, wherein the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to press and displace the tissue, the output step is a step of receiving a first reception signal based on the reflected wave from the tissue as the reception signal by the reception circuit, and outputting the first reception signal based on the reflected wave from the reception circuit, the evaluation step is a step of calculating the displacement of the tissue based on the ultrasound image obtained from the first reception signal to evaluate the hardness of the tissue via the processor, and the pause period is a period from an end of the transmission of the first transmission signal to a start of a subsequent transmission of the first transmission signal.

19. The operation method of the ultrasound diagnostic system according to claim 13, wherein the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to press and displace the tissue, the operation method further includes a third signal generation step of controlling the transmission circuit to generate a second transmission signal consisting of a detection pulse for detecting the displacement of the tissue after the tissue is displaced, and a second transmission step of transmitting the second transmission signal consisting of the detection pulse from the transmission circuit to the plurality of ultrasound transducers to generate a detection ultrasonic wave, and transmitting the generated detection ultrasonic wave to the tissue, the output step is a step of receiving a second reception signal based on the reflected wave of the detection ultrasonic wave from the tissue as the reception signal by the reception circuit, the evaluation step is a step of calculating the displacement of the tissue based on the ultrasound image obtained from the second reception signal to evaluate the hardness of the tissue via the processor, and the pause period is a period from an end of the transmission of the second transmission signal to a start of a subsequent transmission of the first transmission signal.

20. The operation method of the ultrasound diagnostic system according to claim 13, wherein the first transmission step is a step of transmitting a first transmission signal consisting of an excitation pulse as the ultrasound generating transmission signal from the transmission circuit to at least some of the plurality of ultrasound transducers, and generating the excitation ultrasonic wave and transmitting the generated excitation ultrasonic wave to the tissue to excite the tissue to generate a shear wave, the operation method further includes a fourth signal generation step of controlling the transmission circuit to generate a third transmission signal consisting of a detection pulse for detecting an acoustic velocity of the shear wave after the shear wave is generated, and a third transmission step of transmitting the third transmission signal consisting of the detection pulse from the transmission circuit to the plurality of ultrasound transducers to generate a detection ultrasonic wave, and transmitting the generated detection ultrasonic wave to the tissue in which the shear wave is generated, the output step is a step of receiving a third reception signal of the reflected wave of the detection ultrasonic wave from the tissue as the reception signal by the reception circuit, the evaluation step is a step of calculating the acoustic velocity of the shear wave based on the third reception signal to evaluate the hardness of the tissue via the processor, and the pause period is a period from an end of the transmission of the third transmission signal to a start of a subsequent transmission of the first transmission signal.

* * * * *